US012584133B2

(12) United States Patent
Sugai et al.

(10) Patent No.: US 12,584,133 B2
(45) Date of Patent: Mar. 24, 2026

(54) ANTISENSE NUCLEIC ACID AND USE THEREOF

(71) Applicant: NIIGATA UNIVERSITY, Niigata (JP)

(72) Inventors: Akihiro Sugai, Niigata (JP); Osamu Onodera, Niigata (JP)

(73) Assignee: NIIGATA UNIVERSITY, Niigata (JP)

( * ) Notice: Subject to any disclaimer, the term of this patent is extended or adjusted under 35 U.S.C. 154(b) by 486 days.

(21) Appl. No.: 18/037,194

(22) PCT Filed: Nov. 15, 2021

(86) PCT No.: PCT/JP2021/041895
§ 371 (c)(1),
(2) Date: May 16, 2023

(87) PCT Pub. No.: WO2022/113799
PCT Pub. Date: Jun. 2, 2022

(65) Prior Publication Data
US 2024/0002856 A1 Jan. 4, 2024

(30) Foreign Application Priority Data

Nov. 30, 2020 (JP) ................................ 2020-198595

(51) Int. Cl.
| | |
|---|---|
| *C07H 21/02* | (2006.01) |
| *A61P 25/28* | (2006.01) |
| *C12N 15/113* | (2010.01) |
| *G01N 33/50* | (2006.01) |

(52) U.S. Cl.
CPC .......... *C12N 15/1137* (2013.01); *A61P 25/28* (2018.01); *G01N 33/5023* (2013.01); *C12N 2310/11* (2013.01)

(58) Field of Classification Search
CPC .......................... C12N 15/113; C12N 2310/11
See application file for complete search history.

(56) References Cited

U.S. PATENT DOCUMENTS

| | | |
|---|---|---|
| 2011/0034447 A1 | 2/2011 | Nonaka et al. |
| 2014/0099660 A1 | 4/2014 | Nonaka et al. |
| 2020/0165610 A1 | 5/2020 | Nagai et al. |
| 2020/0291382 A1 | 9/2020 | Zhang et al. |
| 2021/0009986 A1 | 1/2021 | Zhang et al. |

FOREIGN PATENT DOCUMENTS

| | | | |
|---|---|---|---|
| CA | 2834128 A1 * | 11/2012 | .............. A61P 31/04 |
| EP | 2272955 A1 | 1/2011 | |
| EP | 2272955 | 8/2015 | |
| WO | 2013064934 | 5/2013 | |
| WO | 2019013141 A1 | 1/2019 | |
| WO | 2019060746 | 3/2019 | |

OTHER PUBLICATIONS

Stein (The Journal of Clinical Investigation, 2001, 108, 5, 641-644).*
Nedorezova et al. (Theranostics, 2022, vol. 12, Issue 16, 7132-7157).*
Office Action of EP Application No. 21897773.4, dated Aug. 13, 2025, 14 pages.
Polymenidou, et al., "Long pre-mRNA depletion and RNA mis-splicing contribute to neuronal vulnerability from loss of TDP-43," Nature neuroscience 14.4, 2011, pp. 459-468.
Ayala, et al., "TDP-43 regulates its mRNA levels through a negative feedback loop," The EMBO journal 30.2, 2011, pp. 277-288.
Sugai, et al., "Robustness and vulnerability of the autoregulatory system that maintains nuclear TDP-43 levels: A trade-off hypothesis for ALS pathology based on in silico data," Frontiers in Neuroscience 12, Feb. 2018, 15 pages.
Nishimura, et al., "Nuclear import impairment causes cytoplasmic trans-activation response DNA-binding protein accumulation and is associated with frontotemporal lobar degeneration," Brain 133.6, 2010, pp. 1763-1771.
Fallini, et al., "Traffic jam at the nuclear pore: All roads lead to nucleocytoplasmic transport defects in ALS/FTD," Neurobiology of disease 140, 2020, 13 pages.
Prasad, et al., "Molecular mechanisms of TDP-43 misfolding and pathology in amyotrophic lateral sclerosis," Frontiers in molecular neuroscience 12, 2019, 36 pages.
Yamagishi, et al., "ASO-enhancement of TARDBP exitron splicing mitigates TDP-43 proteinopathies," bioRxiv, 2024, 22 pages.
A. Koyama et al., Increased cytoplasmic TARDBP mRNA in affected spinal motor neurons in ALS caused by abnormal autoregulation of TDP-43, Nucleic Acids Research, 2016, vol. 44, No. 12, 5820-5836.
A. Sugai et al,. Non-genetically modified models exhibit TARDBP mRNA increase due to perturbed TDP-43 autoregulation, Neurobiology of Disease, vol. 130, 104534, 2019.
A. Sugai, Endogeneous TDP-43 Overexpression with Disrupted Autoregulation: Toward an Amyotrophic Lateral Sclerosis Model Niigata Medical Journal, 2015, vol. 129, No. 11, pp. 658-670.
International Search Report of the International Searching Authority issued in International Application No. PCT/JP2021/041895, 7 pages, dated Jan. 11, 2022.

* cited by examiner

*Primary Examiner* — Amy Rose Hudson
(74) *Attorney, Agent, or Firm* — DLA Piper LLP (US)

(57) ABSTRACT

An antisense nucleic acid targeting intron 6 of TDP-43 mRNA, and including a nucleotide sequence complementary to a sequence consisting of 10 or more consecutive bases in a target sequence, wherein the target sequence is the 96th to 330th or 400th to 530th positions of a nucleotide sequence represented by SEQ ID NO:1.

7 Claims, 20 Drawing Sheets

Specification includes a Sequence Listing.

Aggregation ←——→ Function (B)

Aggregation (-) Function (-)

(C)

Aggregation ↓ Function ↑

FIG. 3D

FIG. 4A
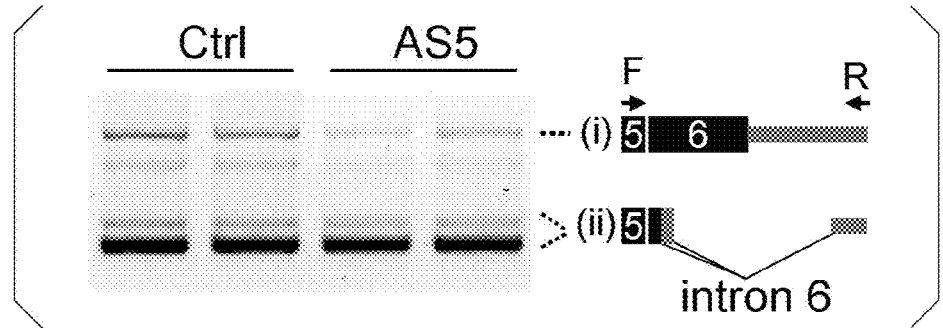
FIG. 4B
FIG. 4C
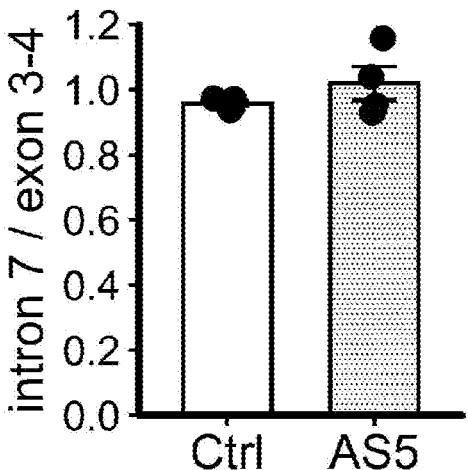

TDP-43

GAPDH

ANTISENSE NUCLEIC ACID AND USE THEREOF

TECHNICAL FIELD

The present invention relates to an antisense nucleic acid and use thereof. Specifically, the present invention provides an antisense nucleic acid, an alternative splicing enhancer of intron 6 of TDP-43 mRNA, a pharmaceutical composition, a screening method for an alternative splicing enhancer of intron 6 of TDP-43 mRNA, and a screening method for a candidate compound for prevention or treatment of TDP-43 proteinopathy.

This application is a 371 of International Application No. PCT/JP2021/041895, filed Nov. 15, 2021, which claims priority to Japanese Patent Application No. 2020-198595, filed in Japan on Nov. 30, 2020, the contents of which are incorporated herein by reference.

SEQUENCE LISTING

This application contains a Sequence Listing which has been submitted in TXT file format and is hereby incorporated by reference in its entirety. Said TXT copy, created on Nov. 15, 2021, is named OSQ17853_Sequence_Listing and is 8,836 bytes in size.

BACKGROUND ART

TDP-43 proteinopathy is a general term for neurodegenerative diseases in which TDP-43 protein aggregates and accumulates, and includes frontotemporal lobar degeneration (FTLD) and amyotrophic lateral sclerosis (ALS). There is no therapeutic drug for FTLD, and symptomatic treatment of various complications is the main treatment. For ALS, edaravone, which aims to eliminate free radicals, and riluzole, which aims to reduce glutamate nerve excitotoxicity, are used as therapeutic agents, but neither of them have a remarkable effect, leading to respiratory muscle paralysis and death in about 2 to 5 years after onset. In addition, for ALS with SOD1 gene mutation, a clinical phase III trial of antisense oligonucleotides aimed at degrading SOD1 mRNA is underway, and for autosomal dominantly inherited ALS, molecule-specific therapeutic methods are undergoing development. However, the cause of sporadic ALS and FTLD, which account for more than 90% of cases, is unknown, and therapeutic agents targeting specific pathological molecules are desired, but the development of such therapeutic agents is extremely difficult.

TDP-43 protein is an RNA-binding protein that is primarily localized to the nucleus, and is involved in diverse RNA metabolisms such as post-transcriptional regulation or the like. TDP-43 proteinopathy is pathologically characterized by loss of TDP-43 protein from the nucleus and accumulation of TDP-43 protein in the cytoplasm, and both the resulting loss of function in the nucleus and acquisition of toxicity in the cytoplasm are involved in pathogenesis. For this reason, it is generally recognized that simply reducing or enhancing the expression of TDP-43 protein is not suitable for therapy.

The intrinsically disordered region (IDR) in TDP-43 protein is the most important region that determines the aggregation property of TDP-43 protein, and its coding region lies in the alternatively spliced intron 6. In addition, TDP-43 protein binds to the 3'UTR of its own pre-mRNA and induces alternative splicing of introns 6 and 7, thereby inducing nonsense-mediated mRNA decay (NMD) and autoregulating expression. The inventors have clarified that in motor neurons of ALS patients in which the nuclear TDP-43 protein is decreased, the autoregulatory function of expression does not work and the TDP-43 mRNA that retains intron 6 is increased (For example, see Non-Patent Document 1). In addition, the inventors have found an antisense oligonucleotide that specifically suppresses alternative splicing of intron 6, and using the antisense oligonucleotide, the inventors have revealed that mRNA including intron 6 was increased, resulting in insolubilization and fragmentation of the TDP-43 protein in the mouse spinal cord, as well as loss of motor neurons (for example, see Non-Patent Document 2). In addition, it was found that in human iPS cell-derived neurons, suppression of alternative splicing of intron 6 decreased nuclear TDP-43 protein (for example, see Non-Patent Document 2). These results showing a pathology similar to ALS suggest that attenuation of alternative splicing of intron 6 is a factor in exacerbating TDP-43 proteinopathy such as ALS pathology due to its increased expression, despite the accumulation of TDP-43 protein in the cytoplasm.

On the other hand, methods of regulating TDP-43 mRNA expression by RNA interference are being investigated in many studies. For example, Patent Document 1 discloses an antisense oligonucleotide for degrading and knocking down TDP-43 mRNA, an antisense oligonucleotide for upregulating expression by targeting the pre-mRNA binding region of the TDP-43 protein itself, and the like.

However, drugs that degrade TDP-43 mRNA cause functional loss of nuclear TDP-43 protein, including in healthy cells, and disrupt cellular functions. On the other hand, drugs that overexpress TDP-43 protein promote cytoplasmic aggregate formation and are cytotoxic. Therefore, drugs targeting the TDP-43 gene are feared to have adverse effects on both diseased and healthy cells, and these drugs are actually used in animal experiments as models for reproducing the pathology. Based on the above, there is a need for drugs that attenuate cytoplasmic aggregate formation while ameliorating nuclear TDP-43 protein depletion in diseased cells, and alter their effects in healthy cells depending on the cell state so as not to exhibit toxicity.

CITATION LIST

Patent Document

[Patent Document 1] PCT International Publication No. WO2019/013141

Non-Patent Document

[Non-Patent Document 1] Koyama, A. et al., "Increased cytoplasmic TARDBP mRNA in affected spinal motor neurons in ALS caused by abnormal autoregulation of TDP-43.", Nucleic Acids Res., Vol. 44, pp. 5820-5836, 2016.

[Non-Patent Document 2] Sugai, A. et al., "Non-genetically modified models exhibit TARDBP mRNA increase due to perturbed TDP-43 autoregulation." Neurobiol. Dis., Vol. 130, 104534, 2019.

SUMMARY OF INVENTION

Technical Problem

The present invention has been made in view of the above circumstances, and provides a novel antisense nucleic acid that enhances alternative splicing of intron 6 of TDP-43 mRNA. The present invention also provides an alternative splicing enhancer of intron 6 of TDP-43 mRNA using the antisense nucleic acid, and a pharmaceutical composition. The present invention also provides a screening method for an alternative splicing enhancer of intron 6 of TDP-43 mRNA, and a screening method for a candidate compound for prevention or treatment of TDP-43 proteinopathy.

Solution to Problem

The present inventors have performed intensive studies to achieve the above object, focusing on isoforms of TDP-43 mRNA, and found that the pathology of TDP-43 proteinopathy can be suppressed by adjusting the expression ratio of these isoforms using an antisense nucleic acid that specifically enhances the alternative splicing of intron 6, thereby leading to the completion of the present invention.

That is, the present invention includes the following aspects.

(1) An antisense nucleic acid targeting intron 6 of TDP-43 mRNA, comprising a nucleotide sequence complementary to a sequence consisting of 10 or more consecutive bases in a target sequence, wherein the target sequence is the 96th to 330th or 400th to 530th positions of a nucleotide sequence represented by SEQ ID NO:1.

(2) The antisense nucleic acid according to (1), comprising a nucleotide sequence represented by any one of SEQ ID NOS: 2 to 7.

(3) An alternative splicing enhancer of intron 6 of TDP-43 mRNA, comprising the antisense nucleic acid according to (1) or (2) as an active ingredient.

(4) A pharmaceutical composition, comprising the antisense nucleic acid according to (1) or (2) as an active ingredient, wherein the pharmaceutical composition is used for prevention or treatment of TDP-43 proteinopathy.

(5) The pharmaceutical composition according to (4), wherein the TDP-43 proteinopathy is frontotemporal lobar degeneration or amyotrophic lateral sclerosis.

(6) A screening method for an alternative splicing enhancer of intron 6 of TDP-43 mRNA, comprising culturing cells expressing TDP-43 mRNA in the presence of a test substance, and quantifying splicing variants not including intron 6 and splicing variants including intron 6 among the TDP-43 mRNA in the cells, wherein a decrease in expression level of the splicing variants including intron 6 in the presence of the test substance compared to that in the absence of the test substance indicates that the test substance is a candidate for the alternative splicing enhancer of intron 6 of TDP-43 mRNA.

(7) A screening method for a candidate compound for prevention or treatment of TDP-43 proteinopathy, comprising culturing cells expressing TDP-43 mRNA in the presence of a test substance, and quantifying splicing variants not including intron 6 and splicing variants including intron 6 among the TDP-43 mRNA in the cells, wherein a decrease in expression level of the splicing variants including intron 6 in the presence of the test substance compared to that in the absence of the test substance indicates that the test substance is a candidate compound for prevention or treatment of TDP-43 proteinopathy.

Advantageous Effects of Invention

The antisense nucleic acid of the above aspect is capable of enhancing alternative splicing of intron 6 of TDP-43 mRNA. The alternative splicing enhancer of the above aspect includes the antisense nucleic acid and is capable of enhancing alternative splicing of intron 6 of TDP-43 mRNA. The pharmaceutical composition of the above aspect contains the antisense nucleic acid and is capable of preventing or treating TDP-43 proteinopathy. According to the screening method of the above aspect, it is possible to screen an alternative splicing enhancer of intron 6 of TDP-43 mRNA. According to the screening method of the above aspect, a candidate compound for prevention or treatment of TDP-43 proteinopathy can be screened.

BRIEF DESCRIPTION OF DRAWINGS

FIG. 1 is a schematic configuration diagram showing isoforms (4 types) of TDP-43 mRNA.

FIG. 2 is a diagram illustrating the aggregation and functionality of TDP-43 protein.

FIG. 3D is an agarose gel electrophoresis image of PCR products obtained by reverse transcription PCR using RNA extracted from human HEK293T cells introduced with each morpholino antisense oligonucleotide and treated with cycloheximide in Example 1.

FIG. 4A is an agarose gel electrophoresis image of PCR products obtained by reverse transcription PCR using RNA extracted from AS5-introduced mouse neuroblastoma Neuro2a cells in Example 2.

FIG. 4B is a graph showing the ratio of the expression level of mRNA in which intron 6 is retained to the expression level of total TDP-43 mRNA in AS5-introduced mouse neuroblastoma Neuro2a cells in Example 2 (in the graph, ***: p<0.001 (two-tailed t-test)).

FIG. 4C is a graph showing the ratio of the expression level of mRNA in which intron 7 is retained to the expression level of total TDP-43 mRNA in AS5-introduced mouse neuroblastoma Neuro2a cells in Example 2.

MODE FOR CARRYING OUT THE INVENTION

Figure 3A:
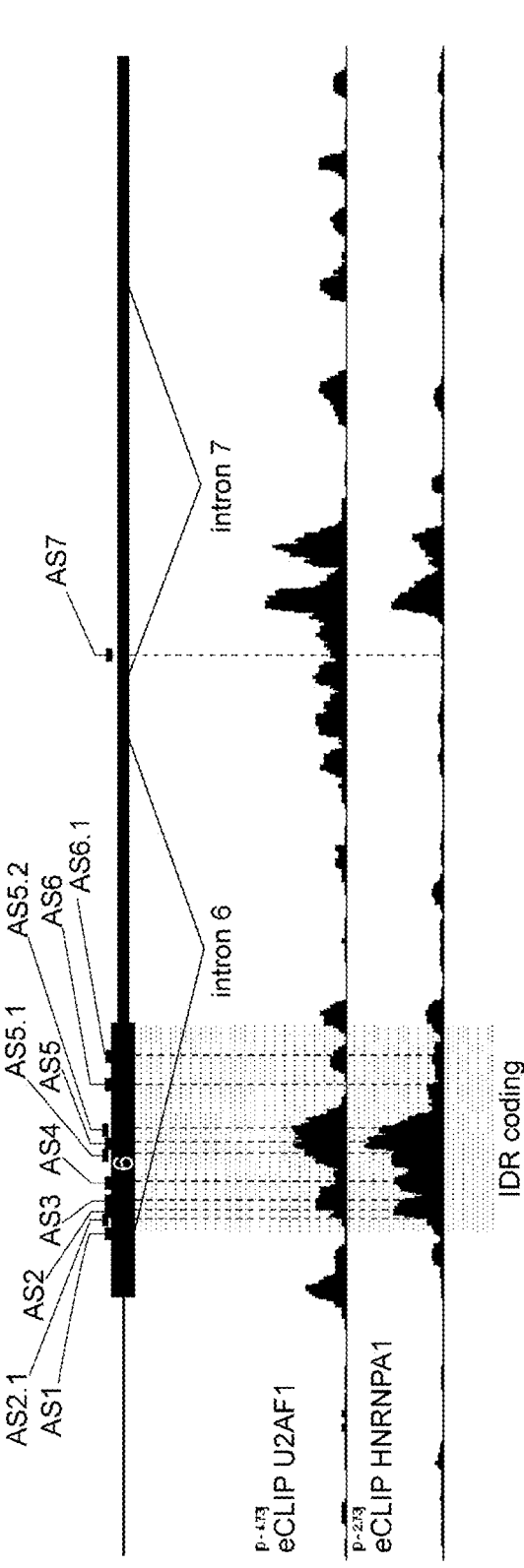
FIG. 3A is a diagram schematically showing the target position of each morpholino antisense oligonucleotide (AS1, AS2.1, AS2, AS3, AS4, AS5, AS5.1, AS5.2, AS6, AS6.1, and AS7) within the sequence of TDP-43 mRNA and the binding positions of U2AF1 and HNRNPA1 in Example 1.

Hereinafter, an antisense nucleic acid, an alternative splicing enhancer of intron 6 of TDP-43 mRNA, a pharmaceutical composition, a screening method for an alternative splicing enhancer of intron 6 of TDP-43 mRNA, and a screening method for a candidate compound for prevention or treatment of TDP-43 proteinopathy will be described in detail.

<TDP-43 Protein>

TDP-43 (TAR DNA-binding protein-43) protein is a protein encoded by the TARDBP gene in humans.

The amino acid sequence of the full-length human TDP-43 protein is disclosed in Genbank Accession No. NP_031401.1.

The nucleotide sequence of the full-length mRNA of human TDP-43 is disclosed in Genbank Accession No. NM_007375.4.

Figure 1:
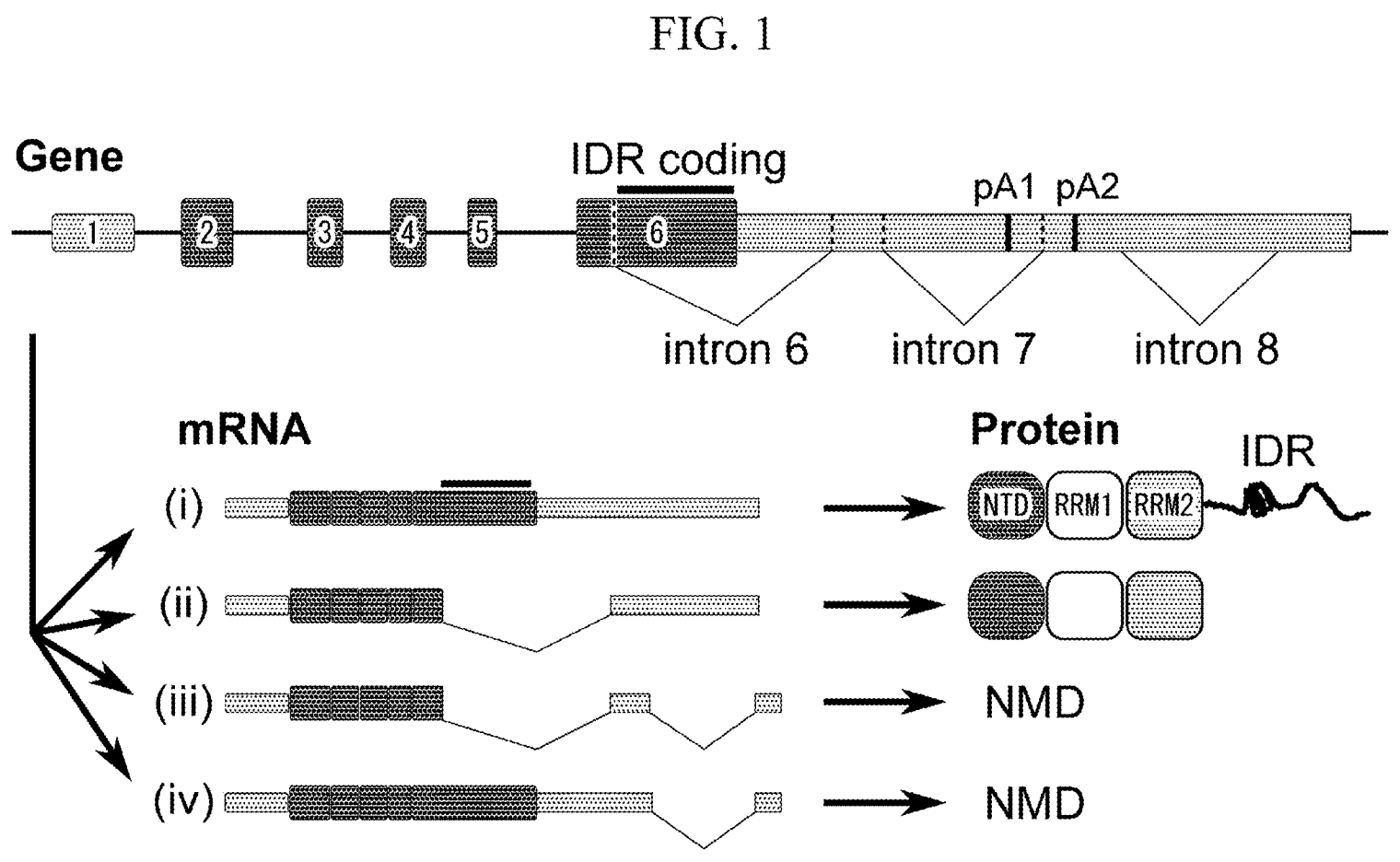

The present inventors have found that the combination of alternative splicing involving the 3'UTR of the pre-mRNA of the TDP-43 gene and the use of alternative polyadenylation sites results in multiple isoforms (splicing variants) in the TDP-43 gene mRNA. These splicing variants can be broadly classified into (i) those in which neither intron 6 nor intron 7 of the TDP-43 gene is spliced (hereinafter sometimes referred to as "variant (i)"), (ii) those in which only intron 6 of the TDP-43 gene is alternatively spliced (hereinafter sometimes referred to as "variant (ii)"), (iii) those in which both intron 6 and intron 7 of the TDP-43 gene are alternatively spliced (hereinafter, may be referred to as "variants (iii)"); and (iv) those in which only intron 7 of the TDP-43 gene is alternatively spliced. These four splicing variants are shown in FIG. 1. Although the autoregulatory mechanisms increase the production of variant (iii) or variant (iv) in response to the expression level of nuclear TDP-43 protein, they are rapidly degraded due to their susceptibility to nonsense-mediated mRNA decay (NMD). Variant (i) in which intron 6 is retained encodes IDR, and the increase in its expression level induces aggregation and results in cytotoxicity.

Figure 2:
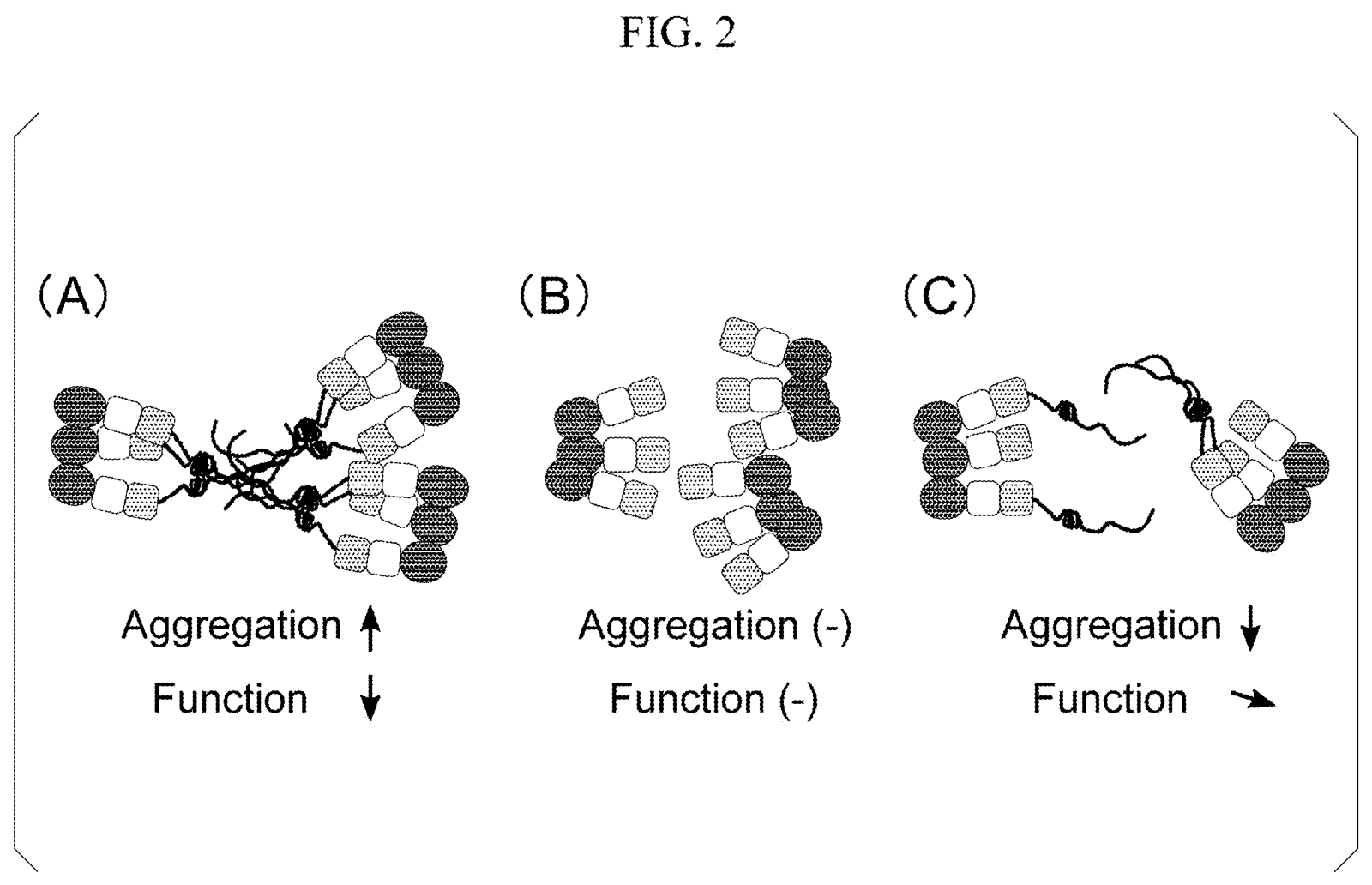

Here, it is believed that in the cells with decreased nuclear TDP-43 protein, inducing alternative splicing of intron 6 only reduces the number of IDR-encoding variants (i) and increases the proportion of variants (ii) in which intron 7 is retained. Variant (ii) is not NMD-sensitive and expresses IDR-lacking TDP-43 protein. It is known that the TDP-43 protein forms oligomers through the N-terminal domain, and its aggregation is strongly dependent on the local concentration of IDR at the C-terminus (see FIG. 2(A)). Therefore, in the cells in which the nuclear TDP-43 protein is reduced, by suppressing the full-length TDP-43 protein expression and producing the TDP-43 protein lacking IDR by inducing alternative splicing of only intron 6, the local concentration of IDR in oligomers is reduced, and the aggregation of TDP-43 protein can be suppressed (see FIG. 2(C)). Suppression of aggregate formation increases the amount of TDP-43 protein that can translocate into the nucleus, resulting in restoration of the function of the nuclear TDP-43 protein. Sufficient restoration of the expression level of the nuclear TDP-43 protein induces alternative splicing of intron 7, resulting in a decreased expression rate of variant (ii) instead of an increased expression rate of variant (iii), and negligible production of IDR-lacking TDP-43 protein, much of which is degraded via NMD.

In addition, TDP-43 intron 6 has a region where the U2AF protein binds, which is important for determining the 3' splicing site. It has been reported that the binding of U2AF in introns suppresses the original splicing together with HNRNPA1 and is involved in intron retention.

Based on these findings, the inventors have designed an antisense nucleic acid that enhances splicing of intron 6 by using the binding region of U2AF and HNRNPA1 as a target sequence, as will be shown in the examples below. Furthermore, the inventors have discovered that in diseased cells, nuclear TDP-43 protein function can be restored and the aggregation in the cytoplasm can be suppressed while in healthy cells, expression of full-length TDP-43 protein can be kept at a non-cytotoxic level by using the antisense nucleic acid targeting the intron 6 of the TDP-43 mRNA designed by applying the autoregulatory mechanism of the TDP-43 protein described above to induce the alternative splicing of only intron 6 and change the composition ratio of each isoform, and completed the present invention.

<Antisense Nucleic Acid>

The antisense nucleic acid of the present embodiment targets intron 6 of TDP-43 mRNA, and includes a nucleotide sequence complementary to a sequence consisting of 10 or more consecutive bases in a target sequence, which is the 96th to 330th or 400th to 530th positions of a nucleotide sequence represented by SEQ ID NO:1.

According to the antisense nucleic acid of the present embodiment, alternative splicing of only intron 6 of TDP-43 mRNA can be induced, and the production of isoforms of mRNA in which neither intron 6 nor intron 7 of the TDP-43 gene is spliced (variant (i) above) can be suppressed. This can suppress aggregation of TDP-43 protein in the cytoplasm and restore the function of the nuclear TDP-43 protein.

The antisense nucleic acid of the present embodiment can be designed with reference to, for example, full-length human TDP-43 mRNA (Genbank Accession No. NM_007375.4).

Specifically, in the sequence of intron 6 (SEQ ID NO: 1) in the full-length human TDP-43 mRNA, the region other than the splicing site (1st, 65th, and 74th positions, which are 5' alternative splicing sites, and 1015th position, which is a 3' alternative splicing site in the nucleotide sequence represented by SEQ ID NO: 1) and to which U2AF1 and HNRNPA1 bind, that is, from the 96th position to the 330th position or from the 400th position to the 530th position of the nucleotide sequence represented by SEQ ID NO: 1, is used as the target sequence.

In the case of targeting TDP-43 mRNA of mammals other than humans as well, the target sequence can be designed with reference to known sequences.

The length of the antisense nucleic acid of the present embodiment is 10 bases or more, preferably 10 bases or more and 50 bases or less, more preferably 15 bases or more and 35 bases or less, and even more preferably 20 bases or more and 30 bases or less.

The antisense nucleic acid of the present embodiment may be composed of DNA, may be composed of RNA, or may be composed of a combination of DNA and RNA. In addition, the antisense nucleic acid of the present embodiment is a nucleotide polymer in which nucleotides are linked by phosphodiester bonds, and may be a polymer of natural nucleotides, a polymer of natural nucleotides and nonnatural nucleotides (natural nucleotide analogues, nucleotides in which at least one of the base moiety, sugar moiety and phosphate moiety is modified (e.g., nucleotides having a phosphorothioate skeleton or a monophorino ring, etc.)), or a polymer of non-natural nucleotides.

Specific examples of the antisense nucleic acid include an antisense nucleic acid consisting of a sequence including any one of the nucleotide sequences represented by any of SEQ ID NOS: 2 to 7. Among them, an antisense nucleic acid consisting of the nucleotide sequence represented by any of SEQ ID NOS: 2 to 7 is preferable.

The antisense nucleic acid of the present embodiment can be synthesized using a known method. Examples of the synthesis methods include synthesis methods using genetic engineering techniques, chemical synthesis methods, and the like. Examples of the synthesis methods using genetic engineering techniques include an in vitro transcription synthesis method, a synthesis method using a vector, a synthesis method using a PCR cassette, and the like.

Examples of the chemical synthesis methods include the phosphoramidite method and the H-phosphonate method. In addition, as the chemical synthesis methods, a method using a commercially available automatic nucleic acid synthesizer can be mentioned.

In addition, the antisense nucleic acid of the present embodiment may be in the form of a vector that expresses the antisense nucleic acid. A vector that expresses an antisense nucleic acid can be produced, for example, by inserting the nucleotide sequence of the target region into a commercially available vector.

Any vector can be used as long as it can express the antisense nucleic acid in the target cells.

The vector can contain a promoter that controls the expression of the antisense nucleic acid. In the vector, the sequence encoding the antisense nucleic acid is functionally linked to a promoter.

The promoter is not particularly limited and, for example, although pol II promoters can be used, pol III promoters are preferable from the viewpoint of more accurate transcription of relatively short nucleic acids. Examples of pol III promoters include, but are not limited to, mouse and human U6-snRNA promoters, human H1-RNase P RNA promoters, human valine-tRNA promoters, and the like. When using the U6 promoter, it is preferable that the 5' end of the antisense nucleic acid be "G" for the transcription initiation. Therefore, it is preferable to design the sequence so that the 5' end of the antisense nucleic acid is "G", or to add "G" to the 5' end of the antisense nucleic acid.

In addition to the antisense nucleic acid coding sequence and promoter, the vector may optionally include an enhancer, a poly (A) addition signal, a marker gene, a replication origin, a gene encoding a protein that binds to the replication origin and controls replication, and the like. The "marker gene" refers to a gene that enables sorting and selection of cells by introducing the marker gene into the cells. Specific examples of the marker gene include drug resistance genes, fluorescent protein genes, luminescent enzyme genes, chromogenic enzyme genes, and the like. These may be used alone or in combination of two or more. Specific examples of the drug resistance gene include puromycin resistance genes, neomycin resistance genes, tetracycline resistance genes, kanamycin resistance genes, zeocin resistance genes, hygromycin resistance genes, chloramphenicol resistance genes, and the like. Specific examples of the fluorescent protein gene include green fluorescent protein (GFP) genes, yellow fluorescent protein (YFP) genes, red fluorescent protein (RFP) genes, and the like. Specific examples of the luminescent enzyme gene include luciferase genes, and the like. Specific examples of the chromogenic enzyme gene include β-galactosidase genes, β-glucuronidase genes, alkaline phosphatase genes, and the like.

The type of vector is not particularly limited, and known expression vectors can be used.

Examples of the expression vectors include plasmid vectors, virus vectors, and the like.

The plasmid vector is not particularly limited as long as it can be expressed in the target cells. For example, in the case of animal cells, commonly used animal cell expression plasmid vectors can be used. Examples of the animal cell expression plasmid vector include, but are not limited to, pX459, pA1-11, pXT1, pRc/CMV, pRc/RSV, pcDNA1/Neo, and the like.

Examples of the viral vector include retrovirus (including lentivirus) vectors, adenovirus vectors, adeno-associated virus vectors, Sendai virus vectors, herpes virus vectors, vaccinia virus vectors, pox virus vectors, polio virus vectors, silbis virus vectors, rhabdovirus vector, paramyxovirus vector, orthomyxovirus vector, and the like.

Among them, a plasmid vector is preferable as the expression vector.

<Alternative Splicing Enhancer>

The alternative splicing enhancer of the present embodiment is an alternative splicing enhancer for intron 6 of TDP-43 mRNA, and contains the aforementioned antisense nucleic acid as an active ingredient.

The alternative splicing enhancer of the present embodiment can effectively induce alternative splicing of intron 6 of TDP-43 mRNA.

For example, the alternative splicing enhancer of the present embodiment containing the antisense nucleic acid is administered to a subject having the TDP-43 gene. The administration method can be carried out by contacting an administration subject with the antisense nucleic acid. Administration may be in vivo or in vitro.

The subjects for administration are not particularly limited, and cells, tissues or organs of mammals such as humans, monkeys, marmosets, mice, rats, guinea pigs, dogs, cats, rabbits, cows, horses, pigs, goats, sheep, and the like can be mentioned.

The alternative splicing enhancer of the present embodiment can further contain a nucleic acid introduction reagent for the purpose of promoting the efficiency of introduction of the antisense nucleic acid into the target cells.

Examples of the nucleic introduction reagent include atelocollagen; liposomes; ionic lipids such as lipofectarnine (registered trademark), lipofectin, transfectam (dioctadecylamidoglycylspermine, DOGS), 1,2-dioleoyl-sn-glycero-3-phosphoethanolamine (DOPE), 1,2-dioleoyl-3-trimethylammonium-propane (DOTAP), didodecyldimethylammonium bromide (DDAB), DHDEAB (N,N-di-n-hexadecyl-N-methyl,N-(2-hydroxyethyl)ammonium bromide), polybrene, poly(ethyleneimine) (PEI) or the like, and the like.

Pharmaceutical Composition

The pharmaceutical composition of the present embodiment is used for prevention or treatment of TDP-43 proteinopathy, and contains the antisense nucleic acid described above as an active ingredient.

According to the pharmaceutical composition of the present embodiment, the accumulation of TDP-43 protein in the cytoplasm can be suppressed and the function of the nuclear TDP-43 protein can be restored, as shown in the Examples below. Therefore, it is effective in preventing or treating TDP-43 proteinopathy.

TDP-43 proteinopathy is a general term for neurodegenerative diseases in which TDP-43 protein aggregates and accumulates, and examples thereof include frontotemporal lobar degeneration (FTLD), amyotrophic lateral sclerosis (ALS) and the like. FTLD and ALS include both genetic variants (familial) and sporadic FTLD and ALS.

In addition, accumulation of TDP-43 protein has been confirmed in neurodegenerative diseases such as Alzheimer's disease, dementia with Lewy bodies, Down syndrome, hippocampal sclerosis, familial british dementia, Perry syndrome, Parkinson's disease, polyglutamine diseases (e.g., Huntington's disease, spinocerebellar degeneration type 3, etc.), myopathies (e.g., sporadic inclusion body myositis, inclusion body myopathy, oculopharyngeal muscular dystrophy, distal myopathy, myofibrillar myopathy, etc.), cerebral corticobasal degeneration, progressive supranuclear palsy, *Argyria granulopathy* or the like, in addition to accumulation of tau protein, amyloid β protein, huntingtin protein or the like. Therefore, it is also applicable to these diseases.

Among these TDP-43 proteinopathies, it is preferably used for the treatment or prevention of FTLD or ALS.

The pharmaceutical composition of the present embodiment may use an effective amount of the antisense nucleic acid alone, or may be formulated and used in combination with a pharmaceutically acceptable carrier.

The antisense nucleic acid contained in the pharmaceutical composition of the present embodiment may be in the form of a nucleic acid molecule, or may be in the form of a vector containing a nucleic acid encoding the antisense nucleic acid as described above or the like, or may be a mixture of these forms.

Examples of the pharmaceutically acceptable carrier include, but are not limited to, excipients such as sucrose, starch or the like; binders such as cellulose, methylcellulose or the like; disintegrants such as starch, carboxymethylcellulose or the like; lubricants such as magnesium stearate, Aerosil or the like; fragrances such as citric acid, menthol or the like; preservatives such as sodium benzoate, sodium bisulfite or the like; stabilizers such as citric acid, sodium citrate or the like; suspending agents such as methylcellulose, polyvinylpyrrolid or the like; dispersants such as surfactants or the like; diluents such as water, saline or the like; base wax, and the like.

The pharmaceutical composition of the present embodiment can further contain a reagent for nucleic acid introduction in order to facilitate the introduction of the antisense nucleic acid into the target cells. As the reagent for nucleic acid introduction, the same reagents as exemplified in the "alternative splicing enhancer" can be used.

Moreover, the pharmaceutical composition of the present embodiment may be a pharmaceutical composition in which the antisense nucleic acid is encapsulated in a liposome. Liposomes are closed microscopic vesicles having an internal phase surrounded by one or more lipid bilayers, and can typically hold water-soluble substances in the internal phase and fat-soluble substances within the lipid bilayers. The term "encapsulation" as used herein includes a state in which the antisense nucleic acid is retained in the liposome internal phase and a state in which the antisense nucleic acid is retained in the lipid bilayer.

The liposomes may be unilamellar or multilamellar. In addition, the particle size of the liposome is, for example, 10 nm or more and 1000 nm or less, preferably 50 nm or more and 300 nm or less. Considering the delivery to the target cells or target tissues, the particle size is more preferably 50 nm or more and 200 nm or less, and even more preferably 50 nm or more and 100 nm or less.

Examples of the method for encapsulating the antisense nucleic acid in liposomes include, but are not limited to, the lipid film method (vortex method), reverse phase evaporation method, surfactant removal method, freeze-thaw method, remote loading method, and the like, and any known methods can be selected as appropriate.

The pharmaceutical composition of the present embodiment can be administered to mammals orally or parenterally, but is preferably administered parenterally. As mammals, the same ones as exemplified in the above "alternative splicing enhancer" can be used.

Examples of the parenteral administration method include subcutaneous injection, intramuscular injection, local injection, intraperitoneal administration, intrathecal administration and the like.

Examples of the formulation suitable for parenteral administration include aqueous and non-aqueous isotonic sterile injection solutions, and the injection solution may further contain antioxidants, buffers, bacteriostatic agents, isotonic agents and the like. Alternatively, aqueous and non-aqueous sterile suspensions can be mentioned, and the injection solutions may further contain suspending agents, solubilizers, thickeners, stabilizers, preservatives and the like.

These formulations can be enclosed in containers such as ampoules and vials in unit doses or multiple doses. Alternatively, the active ingredient and a pharmaceutically acceptable carrier can be lyophilized and stored in such a manner that they can be dissolved or suspended in an appropriate sterile vehicle just prior to use. Other formulations suitable for parenteral administration include sprays and the like.

The content of the antisense nucleic acid in the pharmaceutical composition of the present embodiment is not particularly limited, but can be, for example, approximately 0.1% by mass or more and 100% by mass or less with respect to the total mass of the pharmaceutical composition.

The dosage of the pharmaceutical composition of the present embodiment varies depending on the purpose of administration, administration method, type of target disease, severity and conditions of administration target (sex, age, body weight, etc.), and for example, in the case of systemic administration to adults, a single dose of the antisense nucleic acid can generally be 1 nmol/kg or more and 100 μmol/kg or less. Further, for example, in the case of topical administration to adults, it can be 1 pmol/kg or more and 1 μmol/kg or less. Such a dosage can be administered once or more and 10 times or less. Further, from the viewpoint of maintaining high efficacy of the antisense nucleic acid, additional administration at regular intervals is preferable. The dosing interval is not particularly limited, and for example, may be every day, every three days, every week, every two weeks, every month, every three months, and every six months.

The pharmaceutical composition of the present embodiment can be used in combination with therapeutic agents for TDP-43 proteinopathies such as FTLD or ALS, for example, therapeutic agents for these diseases that are already on the market. Examples of the therapeutic agent include cerebral protective agents (e.g., edaravone, etc.), glutamate action inhibitors (e.g., riluzole, etc.), neurotrophic factors (e.g., insulin-like growth factor-1, 5-HT1a receptor agonists (e.g., zaliproden), etc.), and the like. These concomitant drugs can be formulated together with the pharmaceutical composition of the present embodiment and administered as a single formulation, or can also be formulated separately from the pharmaceutical composition of the present embodiment and administered simultaneously or with a time lag by the same or different administration method as the administration method of the pharmaceutical composition of the present embodiment. In addition, the dosage of these concomitant drugs may be an amount usually used when the drug is administered alone, or may be an amount less than the amount usually used.

<Treatment Method>

In one embodiment, the present invention provides a method of preventing or treating TDP-43 proteinopathy comprising administering to a patient in need of treatment an effective amount of the antisense nucleic acid described above. Here, examples of the antisense nucleic acid include those similar to those described above. TDP-43 proteinopathies include the same ones as those mentioned above, and FTLD or ALS is preferable among them. That is, the method for preventing or treating TDP-43 proteinopathy can also be called a method for preventing or treating FTLD or ALS.

In one embodiment, the invention provides the above antisense nucleic acids for the prevention or treatment of TDP-43 proteinopathy. Here, examples of the antisense nucleic acid include those similar to those described above. TDP-43 proteinopathies include the same ones as those mentioned above, but FTLD or ALS is preferable among them.

In one embodiment, the present invention provides use of the above antisense nucleic acid for manufacturing a pharmaceutical composition for prevention or treatment of TDP-43 proteinopathy. Here, examples of the antisense nucleic acid include those similar to those described above. TDP-43 proteinopathies include the same ones as those mentioned above, and FTLD or ALS is preferable among them.

<Screening Method>

The screening method of the present embodiment is a screening method for a candidate compound for prevention or treatment of TDP-43 proteinopathy, and includes the following steps:

culturing cells expressing TDP-43 mRNA in the presence of a test substance; and quantifying splicing variants not including intron 6 and splicing variants including intron 6 in TDP-43 mRNA in the cells.

A decrease in the expression level of the splicing variant including intron 6 in the presence of the test substance compared to that in the absence of the test substance, or an increase in the expression level of the splicing variant not including intron 6 relative to the expression level of the splicing variant including intron 6, indicates that the test substance is a candidate compound for the prevention or treatment of TDP-43 proteinopathy.

As described above, a substance that reduces the expression level of the splicing variant including intron 6, or a substance that increases the expression level of the splicing variant not including intron 6 relative to the expression level of the splicing variant including intron 6, can be determined to be a candidate compound for prevention or treatment of TDP-43 proteinopathy. Therefore, according to the screening method of the present embodiment, candidate compounds for prevention or treatment of TDP-43 proteinopathy can be screened.

Further, the screening method of the present embodiment can also be a screening method for an alternative splicing enhancer of intron 6 of TDP-43 mRNA.

At this time, a decrease in the expression level of the splicing variant including intron 6 in the presence of the test substance compared to that in the absence of the test substance, or an increase in the expression level of the splicing variant not including intron 6 relative to the expression level of the splicing variant including intron 6, indicates that the test substance is a candidate compound for alternative splicing enhancer of intron 6 of TDP-43 mRNA.

The test substance is not particularly limited, and examples thereof include natural compound libraries, synthetic compound libraries, existing drug libraries, metabolite libraries and the like.

Examples of the cells that express TDP-43 mRNA include, but are not limited to, human HEK293T cells, mouse neuroblastoma Neuro2a cells, induced pluripotent stem cell-derived nerve cells, and the like.

In addition, the screening method of the present embodiment includes screening using the cells treated with cycloheximide, which inhibits degradation of NMD-sensitive mRNA, for the purpose of improving the analysis accuracy. In addition, screening using the cells mimicking the TDP-43 proteinopathy associated with decreased alternative splicing of intron 6 by adding a factor that induces mislocalization of TDP-43, such as by knocking down CSE1L, is also included.

Quantification of the expression levels of the splicing variant not including intron 6 and the splicing variant including intron 6 of TDP-43 mRNA can be performed by, for example, RNA-Seq, quantitative RT-PCR, and the like. In addition, primer sets for detecting splicing variants not including intron 6 and splicing variants including intron 6 of TDP-43 mRNA can be appropriately designed from known sequences. The primer set includes, for example, a combination of a forward primer consisting of the nucleotide sequence represented by SEQ ID NO: 8, a first reverse primer consisting of the nucleotide sequence represented by SEQ ID NO: 9, and a second reverse primer consisting of the nucleotide sequence represented by SEQ ID NO: 10, and the like.

EXAMPLE

The present invention will be described below with reference to Examples, but the present invention is not limited to the following Examples.

Example 1

(Alternative Splicing Enhancing Effect of Intron 6 in Human Cells by Antisense Nucleic Acid)

Six morpholino antisense oligonucleotides (AS2, AS3, AS4, AS5, AS5.1, AS5.2, AS6.1) were designed that targeted U2AF1 and HNRNPA1 binding peaks obtained from the public data of the ENCODE eCLIP experiments (ENCFF811WVR, ENCFF080DPL) shown in FIG. 3A, and two morpholino antisense oligonucleotides (AS2.1, AS6) were designed that detargeted from these binding peaks. A morpholino antisense oligonucleotide targeting a normal splicing site (AS1) and A morpholino antisense oligonucleotide targeting a sequence within intron 7 (AS7) were included in the analysis. A sequence of 25 bases was designed from each target region of 35 bases to 50 bases using the algorithm of GeneTools, LLC. FIG. 3A is a diagram schematically showing the target positions of AS1, AS2.1, AS2, AS3, AS4, AS5, AS5.1, AS5.2, AS6, AS6.1, and AS7 within the sequence of TDP-43 mRNA. In addition, the nucleotide sequences of these antisense nucleic acids are shown in Table 1 below.

TABLE 1

|  | Nucleotide sequence (5'→3') | Sequence number |
|---|---|---|
| AS1 | AAGCCACCTGGATTACCACCAAATC | 11 |
| AS2.1 | CCTCTGCTATTACCAAATCCACCCT | 12 |
| AS2 | TCCACCCCCTCTGCTATTACCAAAT | 2 |
| AS3 | TGATTGTTTCCCAAACCAGCTCCAC | 13 |
| AS4 | TGCTGAACGCACCAAAGTTCATCCC | 3 |
| AS5 | GCTAACATGCCCATCATACCCCAAC | 4 |
| AS5.1 | CATACCCCAACTGCTCTGTAGTGC | 5 |
| AS5.2 | GGTTTTGGTTATTACCCGATGGGCC | 6 |

US 12,584,133 B2

15

TABLE 1-continued

| | Nucleotide<br>sequence (5'→3') | Sequence<br>number |
|---|---|---|
| AS6 | AATTGCTGCACCAGAATTAGAGCCA | 14 |
| AS6.1 | GCCTCCATTAAAACCACTGCCCGAC | 7 |
| AS7 | ACTCCATGAAATAAAGAGTAGCGGA | 15 |

Figure 3B:
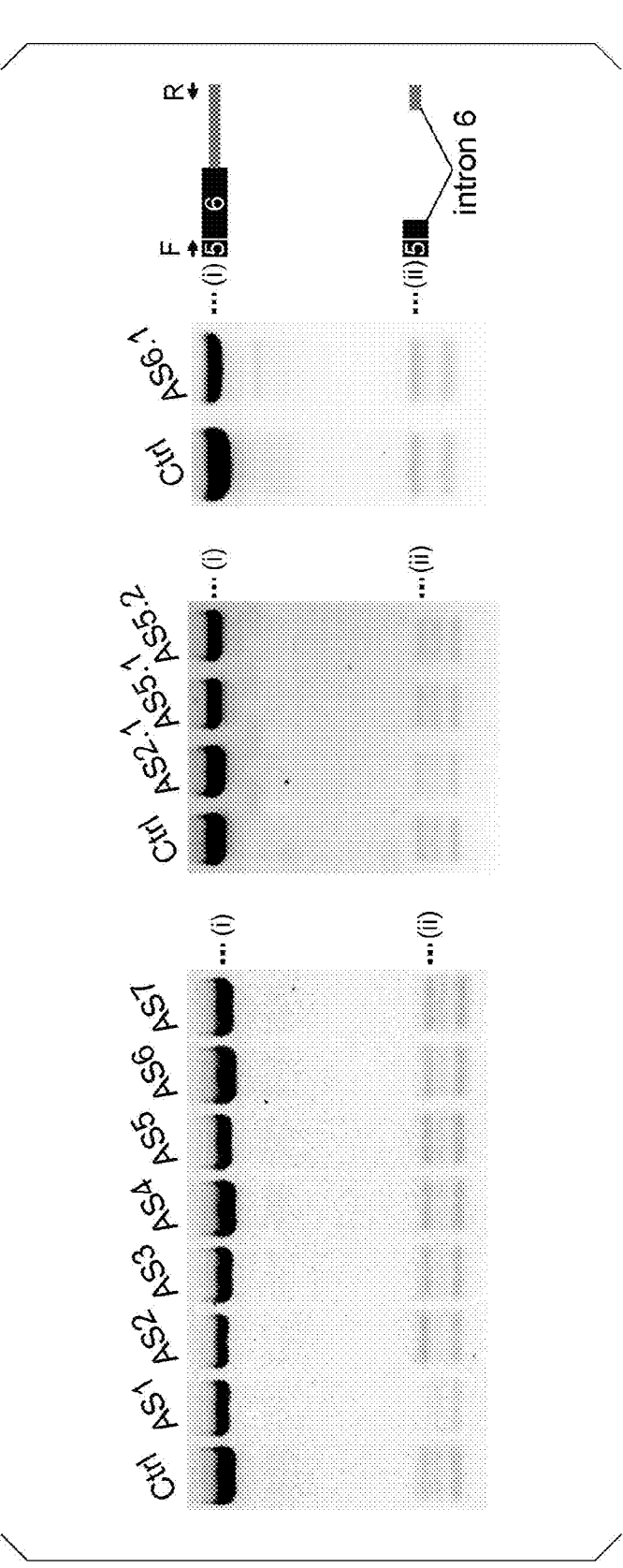
FIG. 3B is an agarose gel electrophoresis image of PCR products obtained by reverse transcription PCR using RNA extracted from human HEK293T cells introduced with each morpholino antisense oligonucleotide in Example 1.

Next, these morpholino antisense oligonucleotides were added to a medium to a concentration of 10 µM, and introduced into human HEK293T using Endo-Porter (manufactured by GeneTools, LLC). In addition, as a control, cells into which a standard control oligo chain was introduced were also prepared. Forty-eight hours after introduction, RNA was extracted from each cell using Nucleospin RNA II (manufactured by Takara Bio Inc.), and the alternative splicing efficiency of intron 6 was examined by reverse transcription PCR. The sequences of the primers used for PCR are shown in Table 2 below. FIG. 3B shows the results of agarose gel electrophoresis of the PCR products, and FIG. 3C shows a graph of the ratio of the expression level of mRNA in which intron 6 was alternatively spliced to the expression level of mRNA in which intron 6 was retained in each cell.

TABLE 2

| | Nucleotide<br>sequence (5'→3') | Sequence<br>number |
|---|---|---|
| Forward primer (F) | GCGCTGTACAGAGGACATGA | 8 |
| Reverse primer (R) | GCCTGTGATGCGTGATGA | 9 |
| Reverse primer (R2) | AGTTCCATCTCAAAAGGGTC | 10 |

Figure 3C:
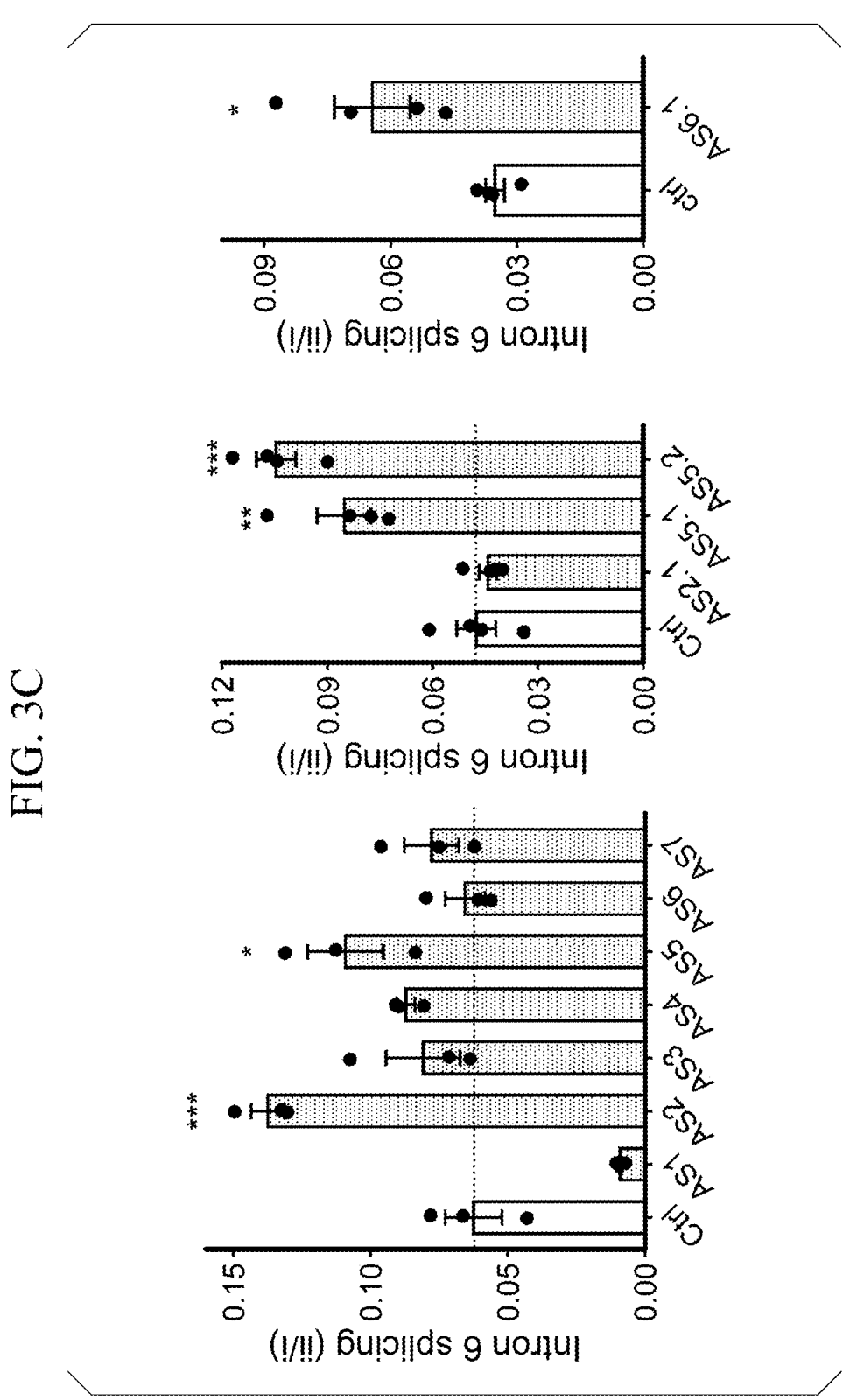
FIG. 3C is a graph showing the ratio of the expression level of mRNA in which intron 6 is alternatively spliced to the expression level of mRNA in which intron 6 is retained, in human HEK293T cells introduced with each morpholino antisense oligonucleotide in Example 1 (in the graph, *: p<0.05, : p<0.01, *: p<0.001 (comparison with control group, Dunnett test)).

As shown in FIGS. 3B and 3C, it was confirmed that in five types of morpholino antisense oligonucleotides (AS2, AS4, AS5, AS5.1, AS5.2, and AS6.1), the splicing was increased and the expression level of mRNA in which intron 6 was retained was decreased.

Figure 3D:
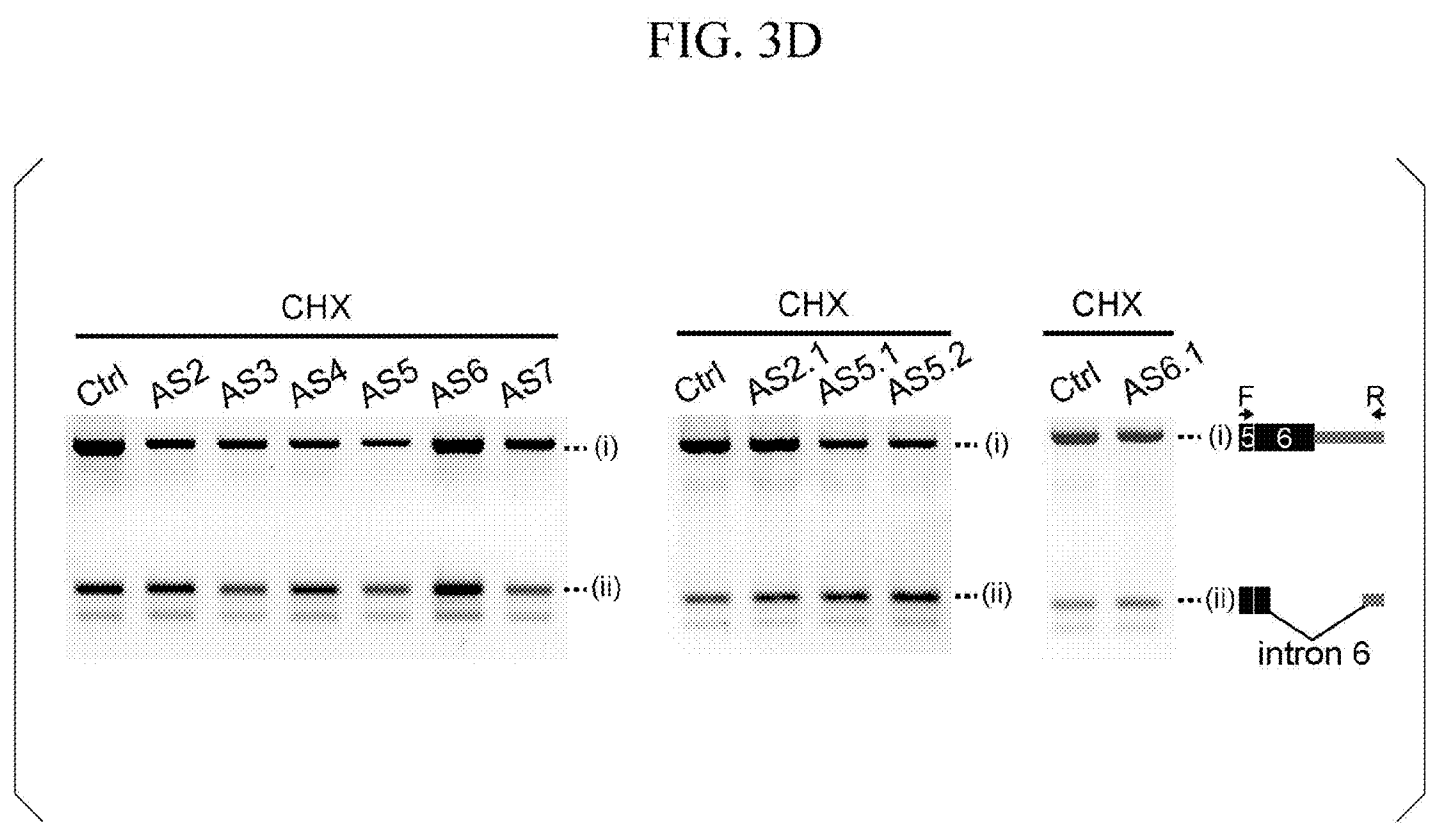
Figure 3E:
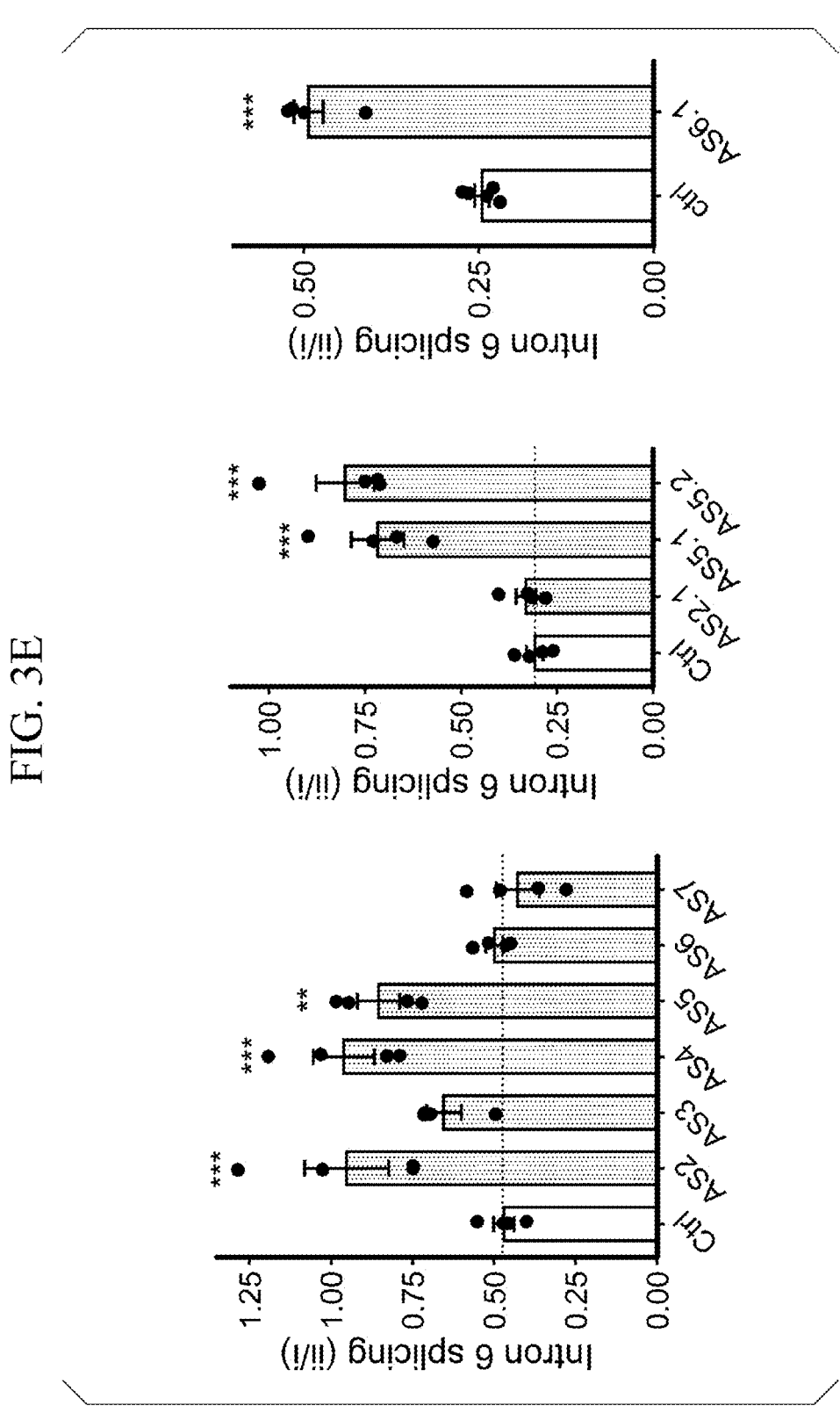
FIG. 3E is a graph showing the ratio of the expression level of mRNA in which intron 6 is alternatively spliced to the expression level of mRNA in which intron 6 is retained, in human HEK293T cells introduced with each morpholino antisense oligonucleotide and treated with cycloheximide in Example 1 (in the graph, : p<0.01, *: p<0.001 (comparison with control group, Dunnett test)).

In order to enhance the quantification of spliced mRNA, cycloheximide treatment was performed from 6 hours before RNA extraction, and the results of similar analysis are shown in FIGS. 3D and 3E. It was confirmed that in five types of morpholino antisense oligonucleotides (AS2, AS4, AS5, AS5.1, AS5.2, and AS6.1), the splicing of intron 6 was enhanced and the expression level of mRNA in which intron 6 was retained was decreased.

Next, the alternative splicing enhancement effect of morpholino antisense oligonucleotides was examined in a state mimicking TDP-43 proteinopathy in which nuclear TDP-43 was decreased and cytoplasmic TDP-43 was accumulated. Specifically, in HEK293T cells, CSE1L involved in nuclear translocation of TDP-43 was knocked down by RNA interference (On-TARGETplus siRNA, manufactured by Dharmacon Inc.) using Lipofectamine RNAiMAX (manufactured by Invitrogen Corporation). Then, after 48 hours, NE-PER Nuclear and Cytoplasmic Extraction Reagents (manufactured by Thermo Scientific) were used to extract proteins from the nuclear and cytoplasmic fractions. An anti-LaminB1 antibody (manufactured by Medical & Biological Laboratories Co., Ltd., PM064) was used as a loading control for the nuclear fraction, and an anti-GAPDH antibody (manufactured by Medical & Biological Laboratories Co., Ltd., M171-3) was used as a loading control for the cytoplasmic fraction. Anti-CSE1L antibody (manufactured by Abcam, ab151546) was used to confirm the expression of CSE1L, and TDP-43 expression in each fraction was analyzed by Western blotting using an anti-TDP-43 antibody (manufactured by Proteintech, 12892-1-AP). The results are shown in FIG. 3F.

Figure 3F:
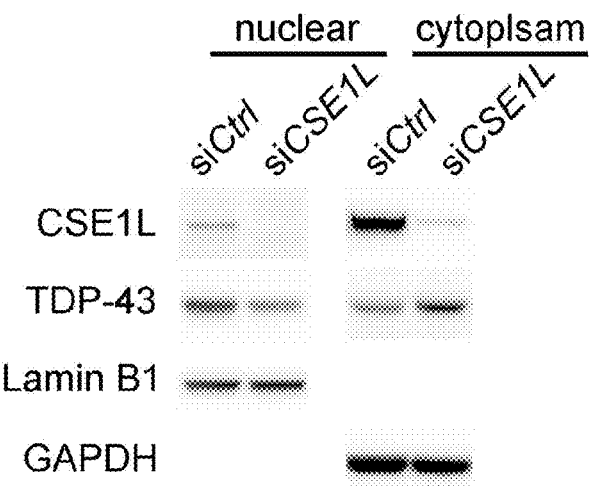
FIG. 3F is Western blotting of nuclear and cytoplasmic fractions of CSE1L-knockdown human HEK293T cells in Example 1.

As shown in FIG. 3F, reduction of CSE1L resulted in a decrease in TDP-43 in the nucleus and an increase in the cytoplasm.

Next, 18 hours after the introduction of siRNA against CSE1L, each of five types of morpholino antisense oligonucleotides (AS2, AS4, AS5, AS5.1, and AS5.2) was introduced and treated with cycloheximide (concentration in the medium: 100 µg/mL, treatment time: 6 hours). Splicing of intron 6 and intron 7 was analyzed by reverse transcription PCR in the same manner as described above. The sequences of the primers used for PCR are shown in Table 2 above. The results of agarose gel electrophoresis of the PCR products are shown in FIG. 3G, a graph showing the ratio of the expression level of mRNA (ii) in which intron 6 was alternatively spliced to the expression level of mRNA (i) in which intron 6 was retained in each cell is shown in FIG. 3H, and the ratio of the expression level of mRNA (v) in which only intron 6 was alternatively spliced to the expression level of mRNA (iii) in which introns 6 and 7 were alternatively spliced in each cell is shown in FIG. 3I.

Figure 3G:
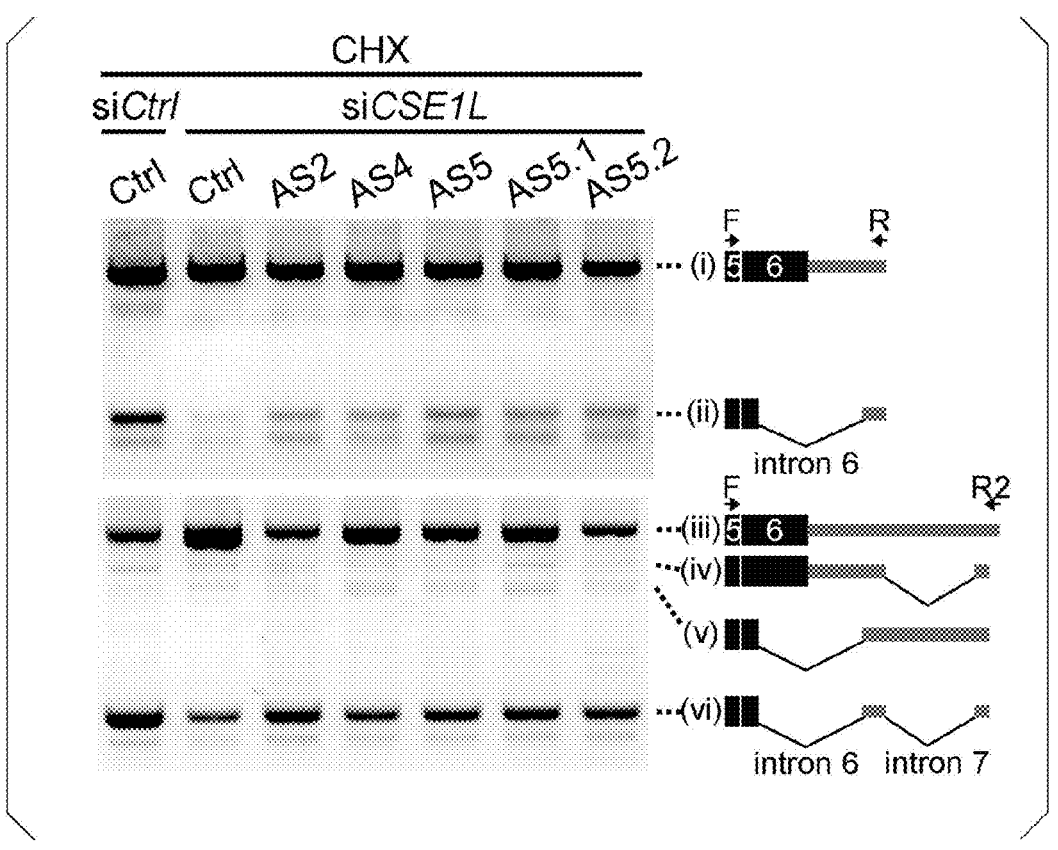
FIG. 3G is an agarose gel electrophoresis image of PCR products obtained by reverse transcription PCR using RNA extracted from human HEK293T cells introduced with each morpholino antisense oligonucleotide and treated with cycloheximide after knocking down CSE1L in Example 1.
Figure 3H:
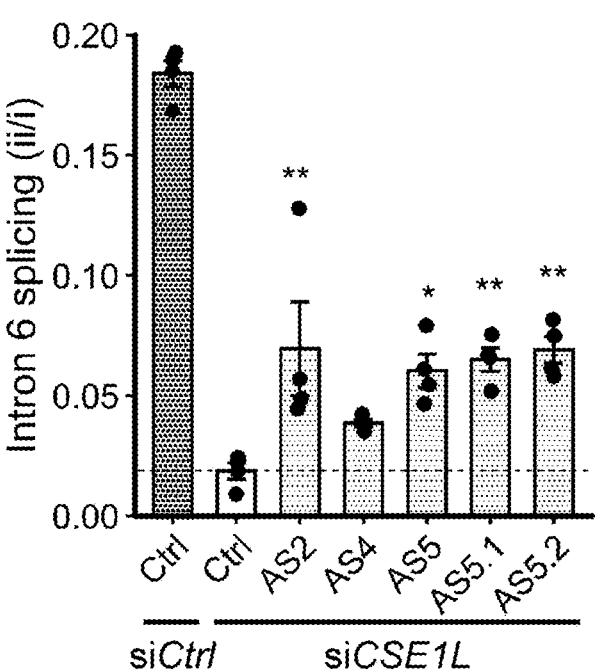
FIG. 3H is a graph showing the ratio of the expression level of mRNA in which intron 6 is alternatively spliced to the expression level of mRNA in which intron 6 is retained, in human HEK293T cells introduced with each morpholino antisense oligonucleotide and treated with cycloheximide after knocking down CSE1L in Example 1 (in the graph, *: p<0.05, : p<0.01, *: p<0.001 (siCSE1L group compared with control group, Dunnett test)).

As shown in the upper part of FIG. 3G and FIG. 3H, in the cells into which the control morpholino antisense oligo was introduced, the splicing of intron 6 was attenuated by CSE1L knockdown. In contrast, 4 morpholino antisense oligos (AS2, AS5, AS5.1, AS5.2) inhibited a decrease in splicing of intron 6.

Figure 3I:
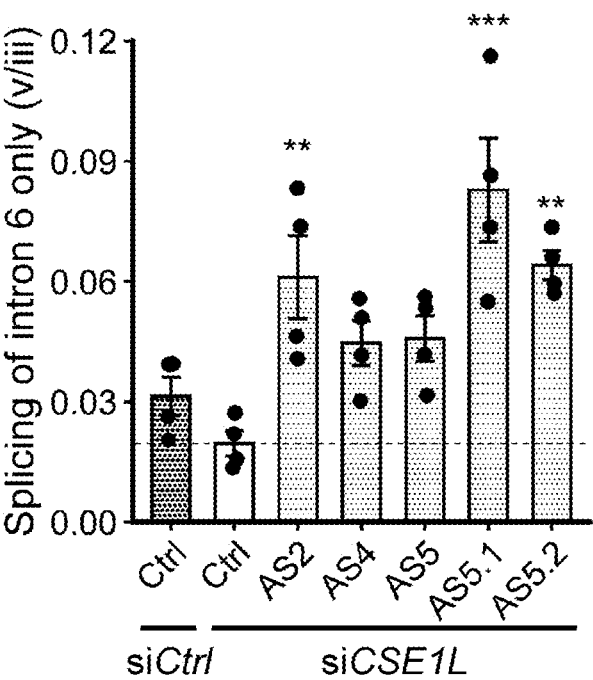
FIG. 3I is a graph showing the ratio of the expression level of mRNA in which only intron 6 is alternatively spliced to the expression level of mRNA in which intron 6 and intron 7 are retained, in human HEK293T cells introduced with each morpholino antisense oligonucleotide and treated with cycloheximide after knocking down CSE1L in Example 1 (in the graph, : p<0.01, *: p<0.001 (siCSE1L group compared with control group, Dunnett test)).

In addition, as shown in the lower part of FIG. 3G and FIG. 3I, 3 types of morpholino antisense oligos (AS2, AS5.1, AS5.2) suppressed an increase in mRNA in which intron 6 and intron 7 were retained, and increased the proportion of the mRNA in which only intron 6 was spliced.

Example 2

(Alternative Splicing Enhancing Effect of Intron 6 in Mouse Cells by Antisense Nucleic Acid)

Among the four types of morpholino antisense oligonucleotides confirmed to have an alternative splicing enhancing effect of intron 6 in human HEK293T cells in Example 1, one type of morpholino antisense oligonucleotide (AS5) having the same target sequence as mouse TDP-43 mRNA was added so that the concentration in the medium was 10 µM, and Endo-Porter (manufactured by GeneTools, LLC) was used to introduce into Neuro2a cells derived from mouse neuroblastoma. Also, cells into which no morpholino antisense oligonucleotide was introduced were also prepared as a control. Forty-eight hours after the introduction, RNA was extracted from each cell using Nucleospin RNA II (manufactured by Takara Bio Inc.), and the alternative splicing efficiency of intron 6 was examined by reverse transcription PCR. The sequences of the primers used in the reverse transcription PCR method are shown in Table 3. The results of agarose gel electrophoresis of the PCR products are shown in FIG. 4A. In addition, FIG. 4B shows a graph of the ratio of the expression level of mRNA in which intron 6 was retained to the expression level of total TDP-43 mRNA in each cell by the droplet digital PCR method. FIG. 4C shows a graph of the ratio of the expression level of mRNA in which intron 7 was retained to the expression level of total TDP-43 mRNA in each cell. Table 4 shows the primer sequences used in the droplet digital PCR method.

TABLE 3

| | Nucleotide sequence (5'→3') | Sequence number |
|---|---|---|
| Forward primer | CAGAGCTTTTGCCTTCGTCA | 16 |
| Reverse primer | CAAAGACGCAGCCTGTGC | 17 |

TABLE 4

| | | Nucleotide sequence (5'→3') | Sequence number | |
|---|---|---|---|---|
| Exon 3- Exon 4 (Total mRNA) | Forward primer (F) | AACTGAGCAGGATCTG AAAGAC | 18 | |
| | Reverse primer | CGAACAAAGCCAAACC CTTTC | 19 | |
| | Probe | 56-FAM/TGGAGAGG T/ZEN/TCTTATGGTT CAGGTCA/3IABkFQ | 20 (5' side) 21 (3' side) | |
| Intron 6 | Forward primer | AGGTGGCTTTGGGAAT CAG | 22 | |
| | Reverse primer | CACCAAAGTTCATCCC TCCA | 23 | |
| | Probe | 5HEX/TGGAGCTGG/ ZEN/CTTGGGAAATAA CCA/3IABkFQ | 24 (5' side) 25 (3' side) | |
| Intron 7 | Forward primer | TGCTGTATGGTGTGTG TTCTC | 26 | |
| | Reverse primer | CCACAAGCTCAGTCCA TGTT | 27 | |
| | Probe | 56-FAM/AGTGTGGG A/ZEN/ACGTGAACTG AAGCT/3IABkFQ | 28 (5' side) 29 (3' side) | |

Figure 4D:
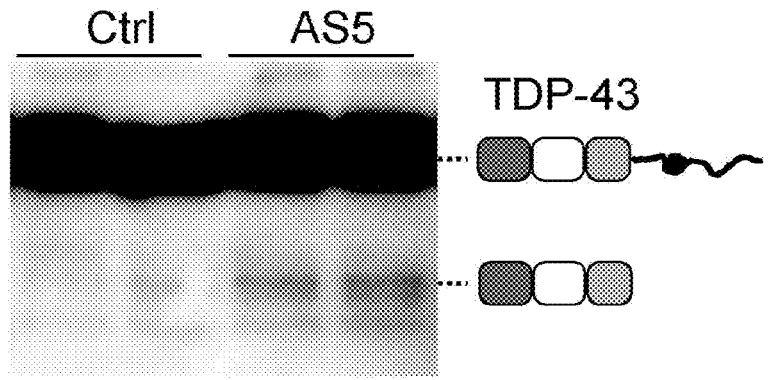
FIG. 4D is a diagram showing the results of Western blotting analysis using a polyclonal antibody whose antigen is the N-terminal side of TDP-43 protein in AS5-introduced mouse neuroblastoma Neuro2a cells in Example 2.

Furthermore, protein was extracted from each cell using RIPA buffer, and the expression of TDP-43 protein was confirmed by Western blotting using a polyclonal antibody (manufactured by Proteintech, 10782-2-AP) whose antigen was the N-terminal side of TDP-43 protein. The results are shown in FIG. 4D.

As shown in FIG. 4A, it was confirmed that the alternative splicing of intron 6 was increased, similar to the results in human HEK293T cells.

As shown in FIG. 4B, the proportion of mRNAs in which alternative intron 6 was retained among all isoforms of TDP-43 mRNA was decreased to an average of 57%.

On the other hand, as shown in FIG. 4C, the mRNA in which intron 7 was retained remained unchanged.

From these results, it was confirmed that the effect of AS5 was an intron 6-specific splicing modification effect.

In addition, as shown in FIG. 4D, in Neuro2a cells introduced with AS5, a TDP-43 protein (~32 kDa), resulting from splicing of intron 6 and lacking an IDR, was produced.

Example 3

(Alternative Splicing Enhancing Effect of Intron 6 in Mouse Central Nervous System)

Figure 5A:
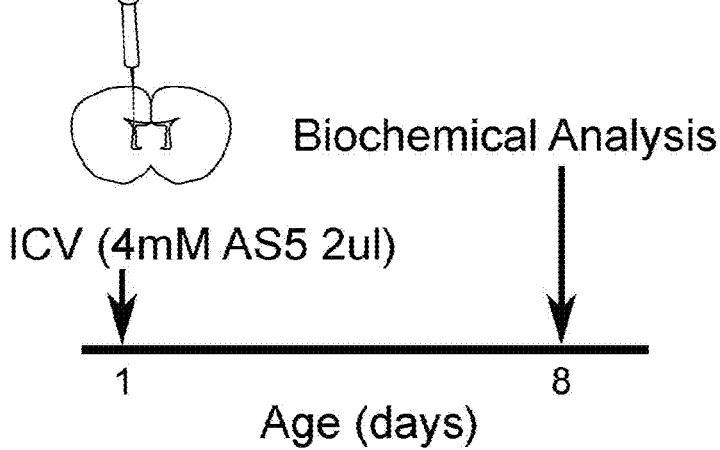
FIG. 5A is a diagram showing a protocol for an intracerebroventricular administration test of AS5 using neonatal mice (C57BL/6NJc1) in Example 3.
Figure 5B:
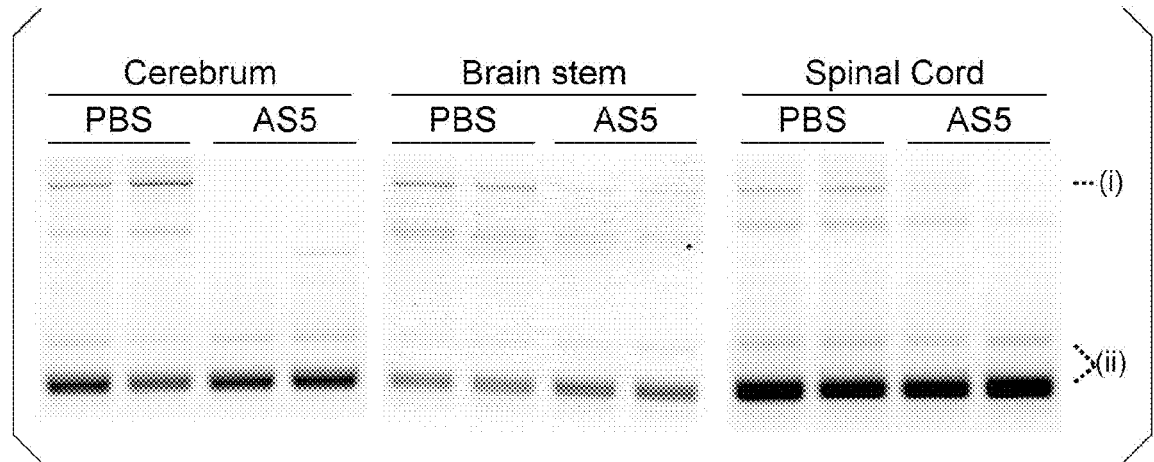
FIG. 5B is an agarose gel electrophoresis image of PCR products obtained by reverse transcription PCR using RNA extracted from each site of the mouse brain to which AS5 was intracerebroventricularly administered in Example 3.
Figure 5C:
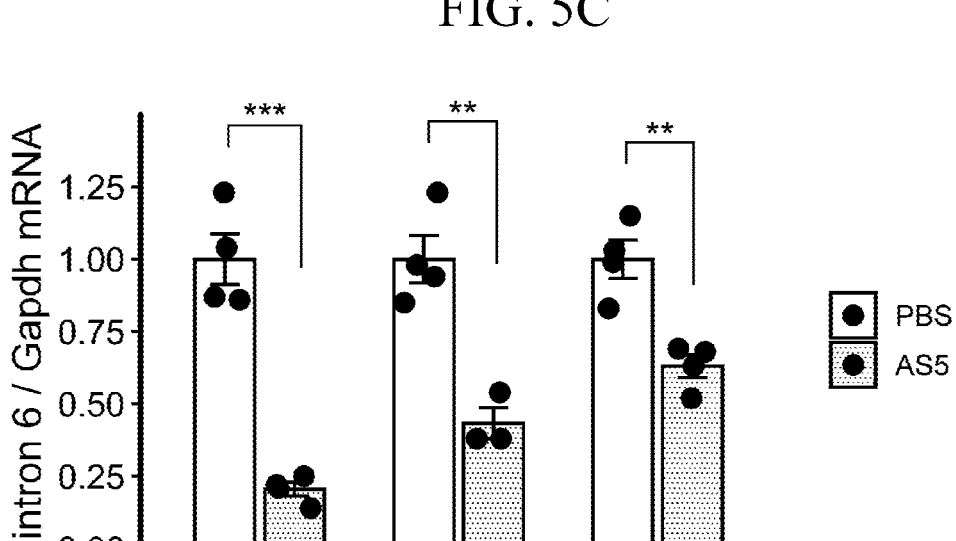
FIG. 5C is a graph showing the expression level of mRNA in which intron 6 is retained in reverse transcription real-time PCR using GAPDH mRNA as a reference gene in each region of the mouse brain to which AS5 was intracerebroventricularly administered in Example 3 (in the graph, : p<0.01, *: p<0.001 (two-tailed t-test)).
Figure 5D:
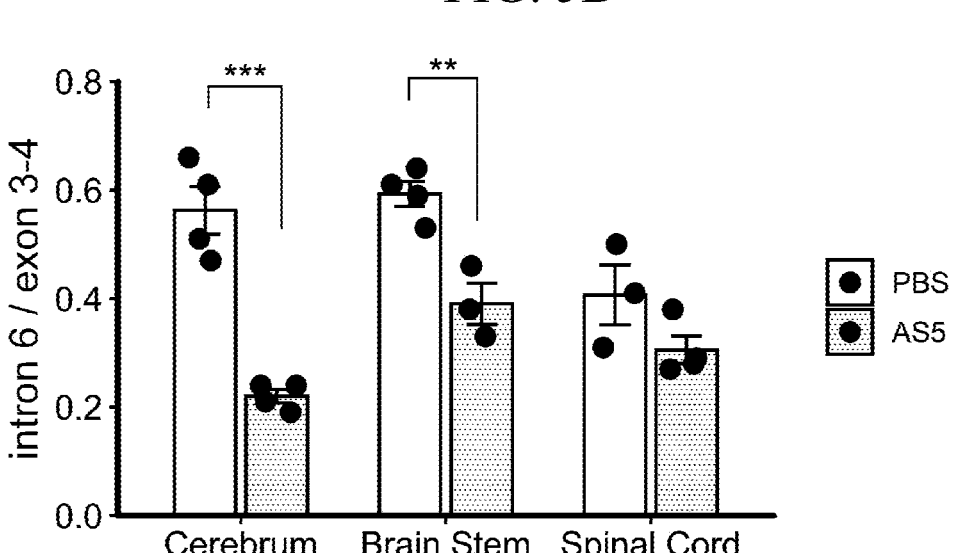
FIG. 5D is a graph showing the ratio of the expression level of mRNA in which intron 6 is retained to the expression level of total TDP-43 mRNA in each region of the mouse brain to which AS5 was intracerebroventricularly administered in Example 3 (in the graph, : p<0.01, *: p<0.001 (two-tailed t-test)).
Figure 5E:
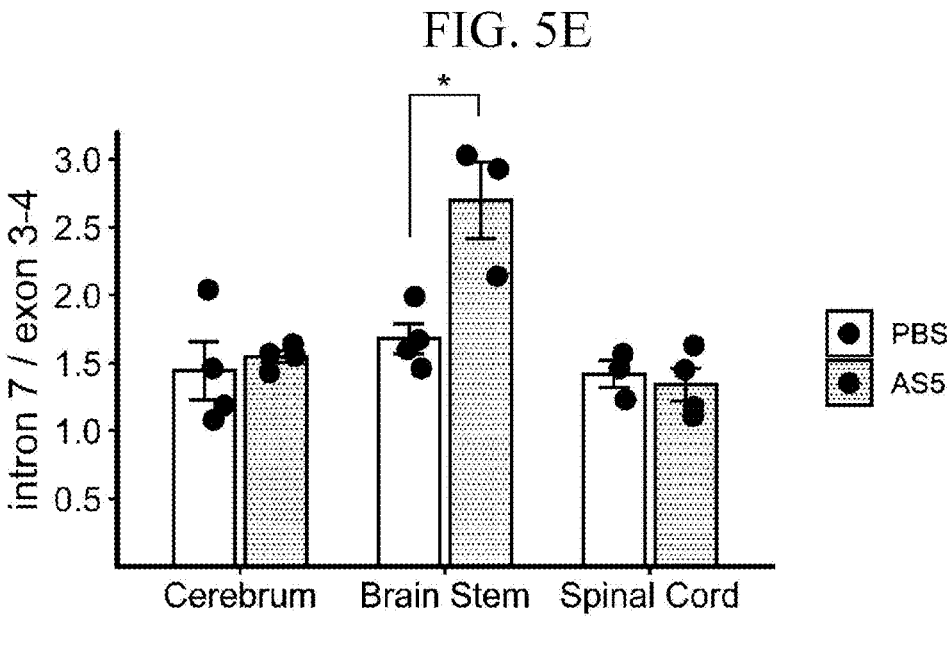
FIG. 5E is a graph showing the ratio of the expression level of mRNA in which intron 7 is retained to the expression level of total TDP-43 mRNA in each region of the mouse brain to which AS5 was intracerebroventricularly administered in Example 3 (in the graph, *: p<0.05 (two-tailed t-test)).

Under hypothermic anesthesia, neonatal mice (C57BL/6NJc1) were injected with a glass capillary into the ventricle under transmitted light, and AS5 (4 mM, 2 uL) designed in Example 1 was administered (see FIG. 5A). In addition, a group to which PBS was similarly administered was also prepared as a control. One week later, RNA in the cerebrum, brain stem, and spinal cord on the side to which AS5 or PBS was administered was extracted using Nucleospin RNA II (manufactured by Takara Bio Inc.), and the alternative splicing efficiency of intron 6 was examined by reverse transcription PCR. The sequences of the primers used for PCR are shown in Table 2 above. FIG. 5B shows the results of agarose gel electrophoresis of the PCR products in each site of the mouse central nervous system, and FIG. 5C shows the results of real-time quantitative PCR showing the expression level of mRNA in which intron 6 was retained, using GAPDH as a reference gene. In addition, FIG. 5D is a graph showing the ratio of the expression level of mRNA in which intron 6 was retained to the expression level of total TDP-43 mRNA by the droplet digital PCR method. FIG. 5E shows a graph of the ratio of the expression level of mRNAs in which intron 7 was retained to the expression level of total TDP-43 mRNA. In addition, Table 5 shows the primer sequences used to detect GAPDH cDNA used in real-time quantitative PCR. Other primer sequences used are as shown in Tables 3 and 4 above.

TABLE 5

| | Nucleotide sequence (5'→3') | Sequence number |
|---|---|---|
| Forward primer | TGTGTCCGTCGTGGATCTGA | 30 |
| Reverse primer | TTGCTGTTGAAGTCGCAGGAG | 31 |

Figure 5F:
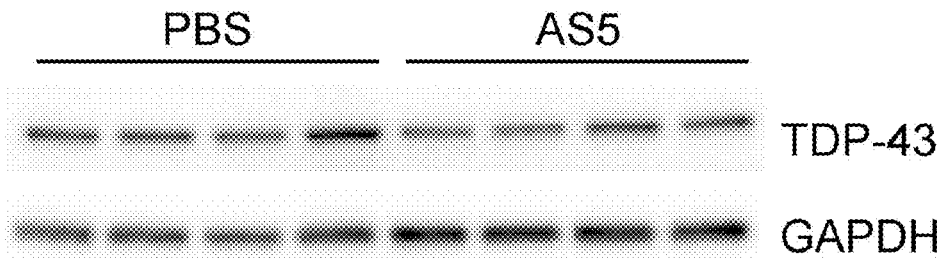
FIG. 5F shows the results of Western blotting analysis using a polyclonal antibody whose antigen is the C-terminal side of the TDP-43 protein and an anti-GAPDH antibody as a control in each region of the mouse brain to which AS5 was intracerebroventricularly administered in Example 3.

Furthermore, protein was extracted from the mouse spinal cord using RIPA buffer, and the expression of TDP-43 protein was confirmed by Western blotting using a polyclonal antibody (manufactured by Proteintech, 12892-1-AP) whose antigen was the C-terminal side of TDP-43 protein and an anti-GAPDH antibody (manufactured by Medical & Biological Laboratories Co., Ltd., M171-3) as a control. FIG. 5F shows the results of Western blotting analysis, and FIG. shows a graph of the expression level of TDP-43 protein corrected by the expression level of GAPDH, quantified from the results of Western blotting analysis. FIG. 5H shows the results of real-time quantitative PCR measurement of the expression level of Aif1 mRNA, which reflects immunoreactive inflammation, in each site of the central nervous system, using GAPDH as a reference gene. In addition, Table 6 shows the primer sequences used to detect Aif1 cDNA used in the real-time quantitative PCR. The primer sequences used to detect the GAPDH cDNA are shown in Table 5 above.

TABLE 6

| | Nucleotide sequence (5'→3') | Sequence number |
|---|---|---|
| Forward primer | ACGAACCCTCTGATGTGGTC | 32 |
| Reverse primer | CGGGATGGAAGAGAGAGGA | 33 |

As shown in FIG. 5B, increased alternative splicing of intron 6 was confirmed.

In addition, a decrease in mRNA in which intron 6 was retained was confirmed (see FIG. 5C). At this time, the proportion of mRNA in which intron 6 was retained was decreased (see FIG. 5D), but the alternative splicing of intron 7 was not decreased (see FIG. 5E).

Figure 5G:
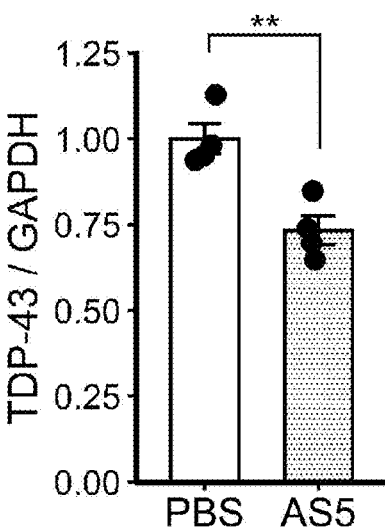
FIG. 5G is a graph showing the ratio of the expression level of TDP-43 protein to the expression level of GAPDH quantified from the results of FIG. 5F (in the graph, **: p<0.01 (two-tailed t-test)).
Figure 5H:
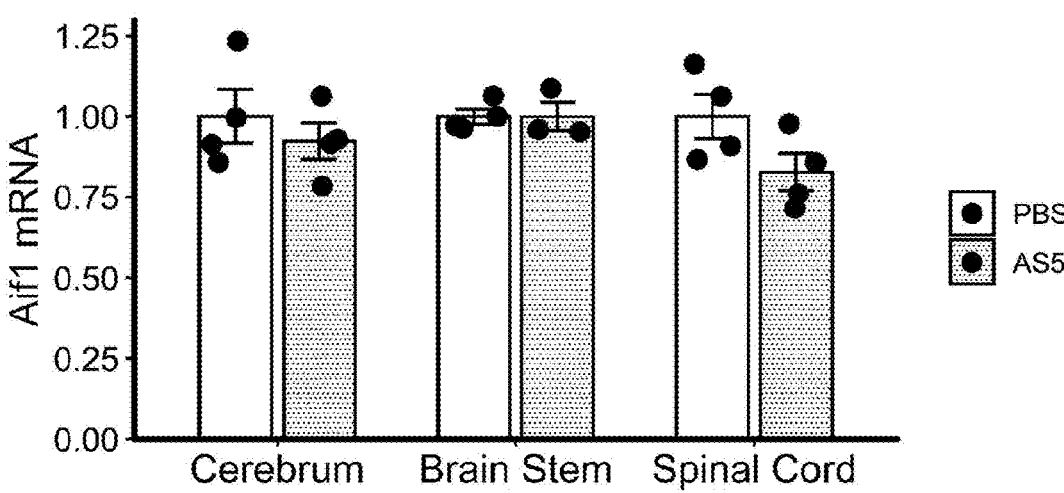
FIG. 5H is a graph showing the expression levels of Aif1 mRNA in the cerebrum, brain stem, and spinal cord after intracerebroventricular administration of AS5 in Example 3.

Furthermore, as shown in FIGS. 5F and 5G, full-length TDP-43 protein was reduced to approximately 70% in the spinal cord.

At this time, there was no difference in Aif1 mRNA expression, which reflects immunoreactive inflammation.

Example 4

(Alternative Splicing Enhancing Effect of Intron 6 in Adult Mouse Spinal Cord and Toxicity Evaluation)

Figure 6A:
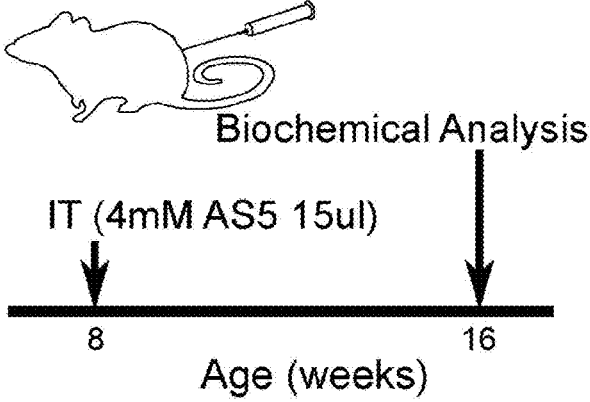
FIG. 6A is a diagram showing a protocol for an intrathecal administration test of AS5 using adult mice (C57BL/6NJc1) in Example 4.
Figure 6B:
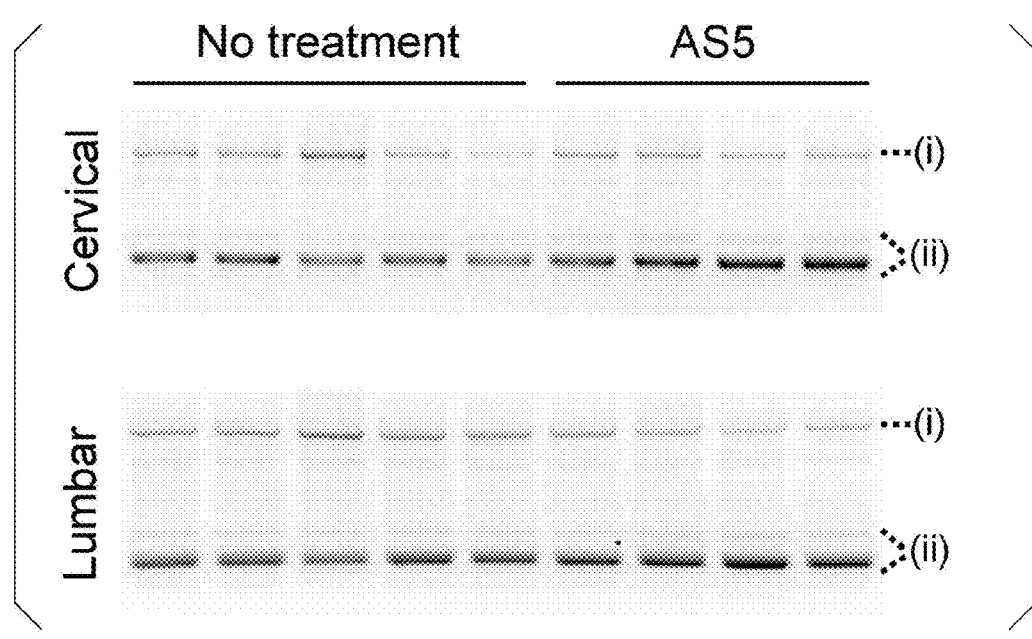
FIG. 6B is an agarose gel electrophoresis image of PCR products obtained by reverse transcription PCR using RNA extracted from the cervical and lumbar spinal cords of mice intrathecally administered with AS5 in Example 4.

AS5 (4 mM, 15 μL) was administered intrathecally to eight-week-old adult mice (C57BL/6NJc1) via lumbar puncture (see FIG. 6A). In addition, an unadministered group was also prepared as a control. Eight weeks after administration, mouse neck and lumbar RNA was extracted using Nucleo-spin RNA II (manufactured by Takara Bio Inc.), and the alternative splicing efficiency of intron 6 was examined by reverse transcription PCR. The sequences of the primers used for PCR are shown in Table 3 above. FIG. 6B shows the results of agarose gel electrophoresis of the PCR products, and FIG. 6C shows a graph of the ratio of the expression level of mRNA in which intron 6 was retained to the expression level of mRNA in which intron 6 was alternatively spliced at each site.

In addition, the body weight and grip power of each of the male and female mice subjected to the administration test were measured. The results are shown in FIG. 6D (body weight) and FIG. 6E (grip power).

Furthermore, the expression level of Aif1 mRNA, which reflects immunoreactive inflammation, was confirmed by reverse transcription real-time PCR in the lumbar spinal cord RNA. GAPDH mRNA was used as a reference gene. The results are shown in FIG. 6F.

Figure 6C:
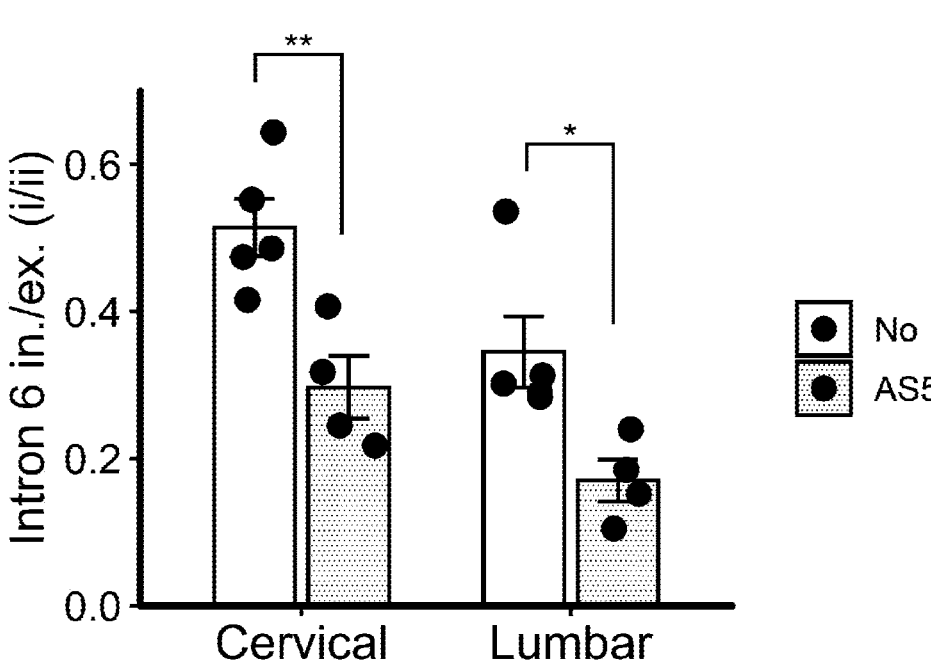
FIG. 6C is a graph showing the ratio of the expression level of mRNA in which intron 6 is retained to the expression level of mRNA in which intron 6 is alternatively spliced in the neck and lumbar spine of mice intrathecally administered with AS5 in Example 4. (in the graph, *: p<0.05, **: p<0.01 (two-tailed t-test)).
Figure 6D:
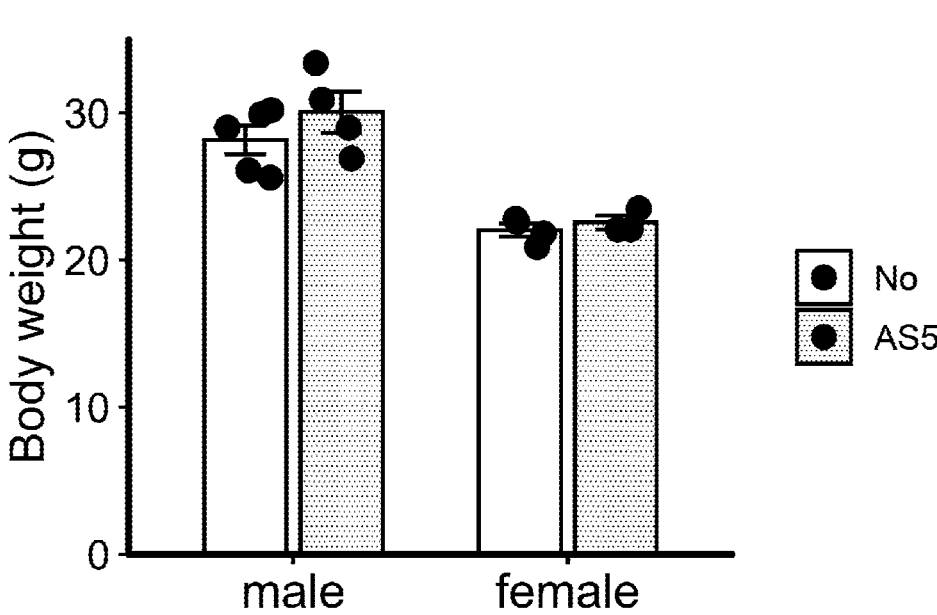
FIG. 6D is a graph showing body weights of male and female mice eight weeks after intrathecal administration of AS5 in Example 4.
Figure 6E:
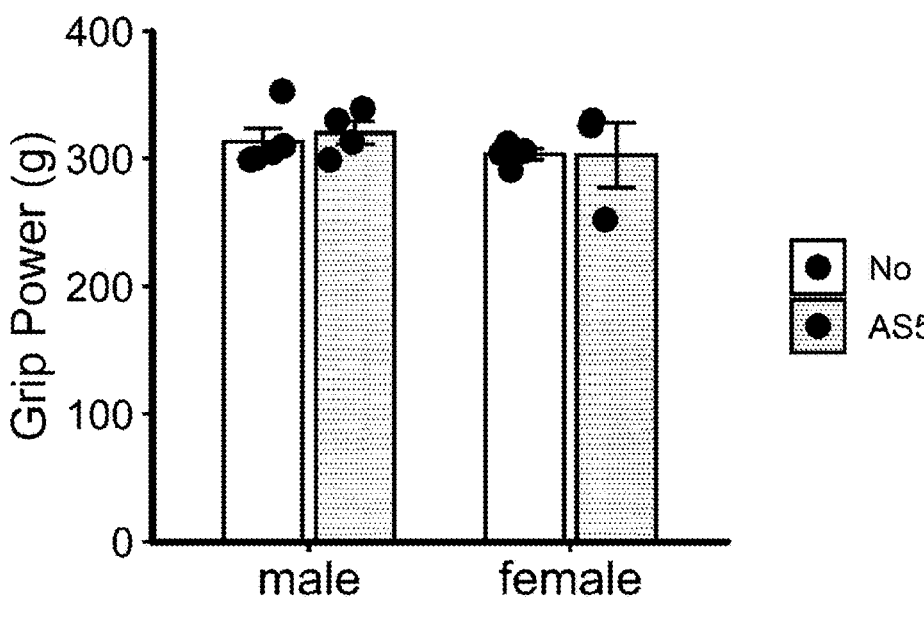
FIG. 6E is a graph showing grip power of male and female mice eight weeks after intrathecal administration of AS5 in Example 4.
Figure 6F:
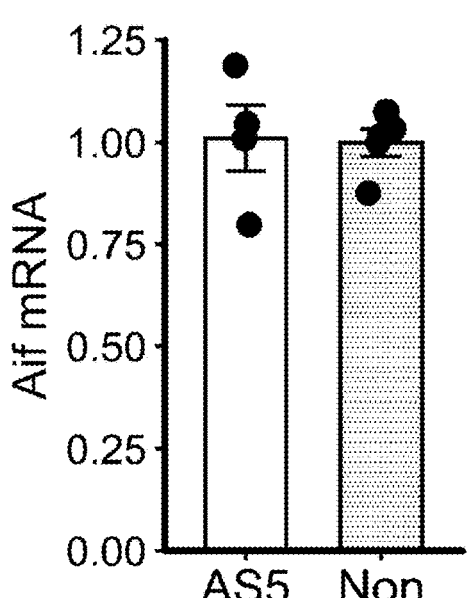
FIG. 6F is a graph showing the expression level of Aif1 mRNA in the lumbar spinal cord eight weeks after intrathecal administration of AS5 in Example 4.

The alternative splicing enhancing effect of intron 6 was maintained until eight weeks after administration (see FIGS. 6B and 6C). In addition, there was no difference in body weight (see FIG. 6D) and grip power (see FIG. 6E) from the PBS-administered group, and there was no difference in the expression of Aif mRNA, which reflects immunoreactive inflammation (see FIG. 6F).

These results suggest that AS5 exerts the expected splicing enhancing effect in the central nervous system of adult mice, but does not have tissue toxicity.

Example 5

(Effect of Prolonging Survival Time on Mouse Model of TDP-43 Proteinopathy)

Figure 7A:
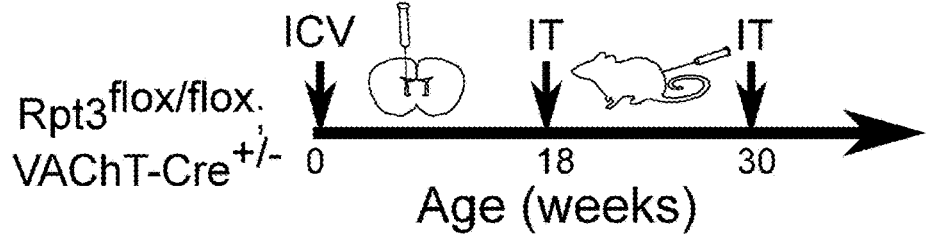
FIG. 7A is a diagram showing protocols for intracerebroventricular and intrathecal administration tests of AS5 using neonatal motor neuron-specific Rpt3 conditional knockout mice (Rpt3$^{flox/flox}$; VAChT-Cre$^{+/-}$) in Example 5.
Figure 7B:
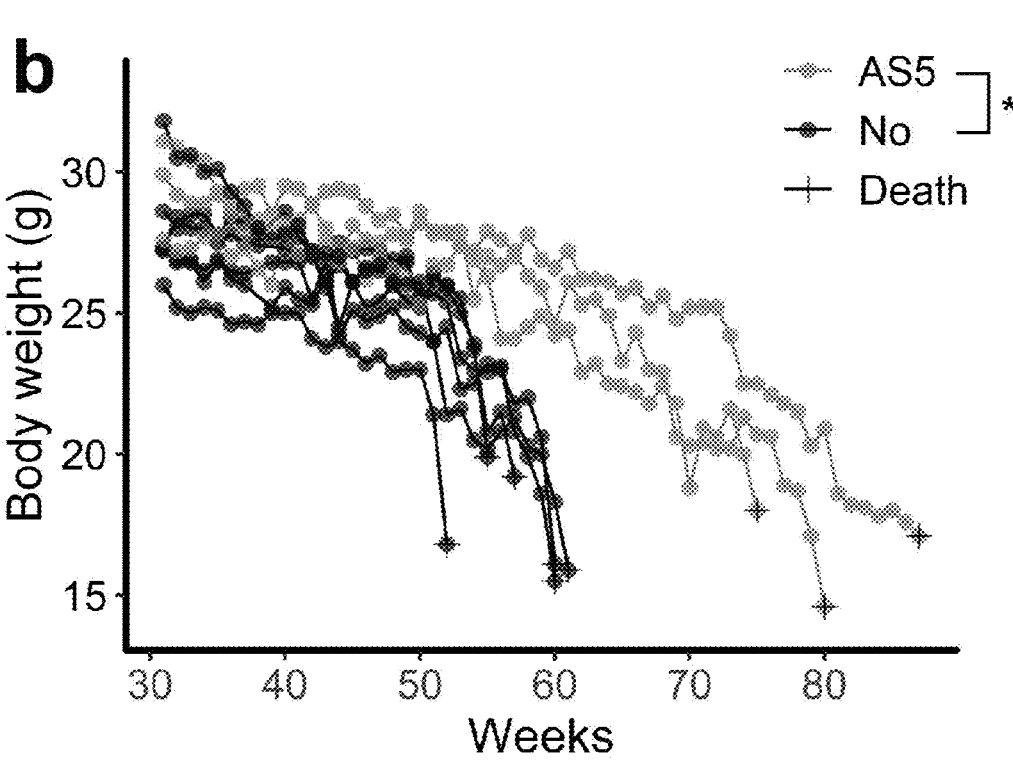
FIG. 7B is a graph showing changes in body weight over time and time to death in AS5-administered mice in Example 5.

AS5 (4 mM, 2 uL) was administered intracerebroventricularly to 3 neonatal motor neuron-specific Rpt3 conditional knockout mice (Rpt3$^{flox/flox}$; VAChT-Cre$^{+/-}$) exhibiting aggregation of TDP-43 protein due to reduced proteasome function, followed by intrathecal administration of AS5 (4 mM, 15 μL) to 18-week-old and 30-week-old mice by lumbar puncture (See FIG. 7A). A group to which AS5 was not administered was also prepared as a control. FIG. 7B is a graph showing changes in body weight over time and time to death in AS5-administered mice.

As shown in FIG. 7B, reduction in body weight loss after 30 weeks and prolongation of survival were confirmed in three AS5-administered mice compared to six AS5-unadministered mice (median survival time: 405.5 days (AS5-unadministered group) vs 558.0 days (AS5-administered group), p-value: Logrank test).

Example 6

(Motor Function Improvement Effect on Mouse Model after Onset of TDP-43 Proteinopathy)

Figures 8A, 8B:
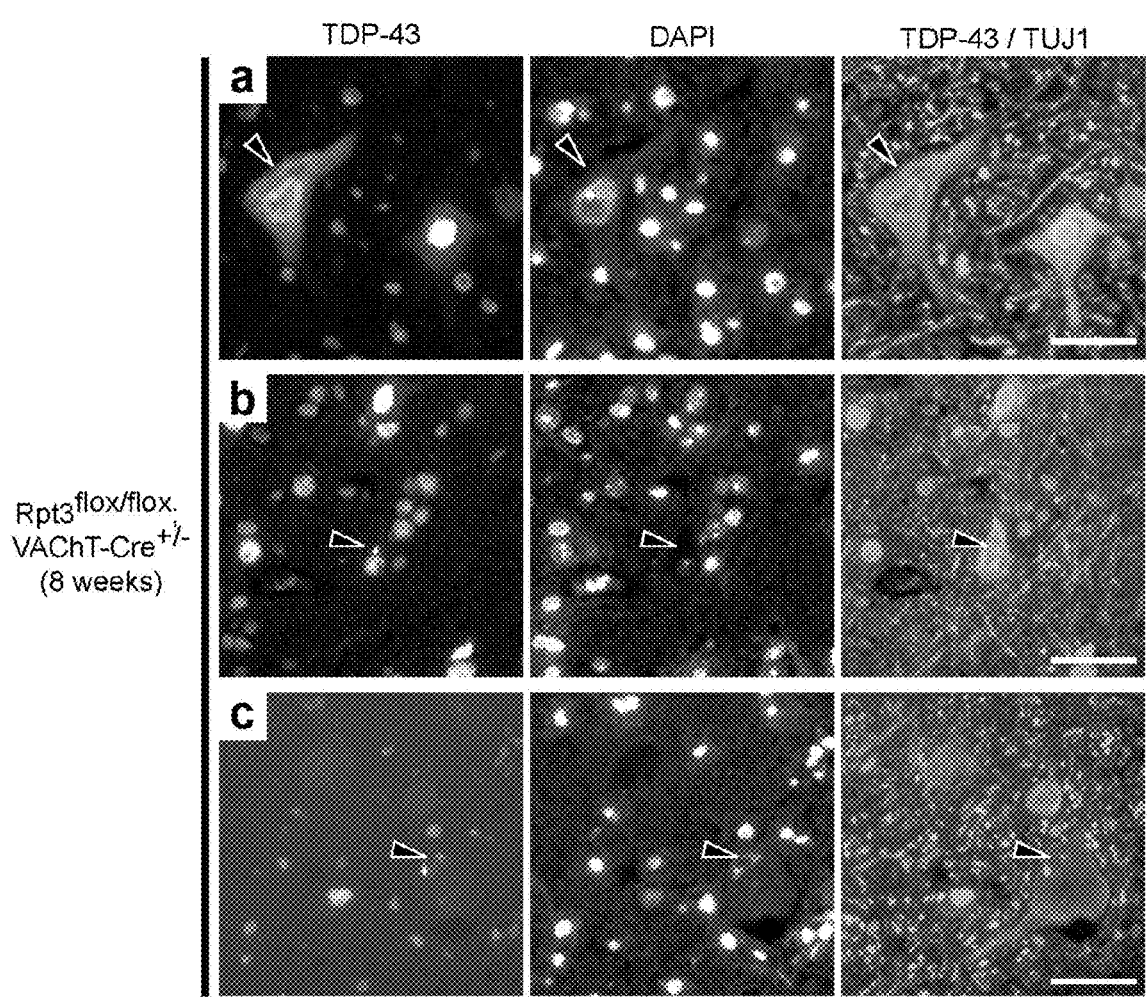
FIG. 8A is an (immuno) stained image with an anti-TDP-43 antibody, 4',6-diamidino-2-phenylindole (DAPI) and an anti-TUJ1 antibody in the spinal cord motor neurons of adult motor neuron-specific Rpt3 conditional knockout mice (Rpt3$^{flox/flox}$; VAChT-Cre$^{+/-}$) in Example 6. Scale bar indicates 40 μm. In the images, "a" to "c" represent patterns observed in TDP-43 proteinopathies in human patients. Specifically, "a" is a stained image of a motor neuron in which nuclear TDP-43 is decreased and TDP-43 is diffusely mislocalized in the cytoplasm. "b" is a stained image of a motor neuron in which aggregates of TDP-43 are observed in the cytoplasm. "c" is a stained image of a motor neuron in which intranuclear TDP-43 has almost disappeared.
FIG. 8B is a diagram showing a protocol for intrathecal administration test of AS5 using adult motor neuron-specific Rpt3 conditional knockout mice (Rpt3$^{flox/flox}$, VAChT-Cre$^{+/-}$) in Example 6.

The effect of AS5 on the adult mice (Rpt3$^{flox/flox}$; VAChT-Cre$^{+/-}$) after the appearance of pathological abnormalities observed in TDP-43 proteinopathy was examined. In this mouse model, it is known that Rpt3 expression in spinal motor neurons disappears at six weeks of age, and disappearance of TDP-43 protein from the nucleus and aggregation in the cytoplasm are observed at eight weeks of age (see FIG. 8A).

Therefore, AS5 (4 mM, 15 μL) was intrathecally administered to eight-week-old and 24-week-old Rpt3$^{flox/flox}$; VAChT-Cre$^{+/-}$ mice by lumbar puncture (see FIG. 8B). In addition, a group in which only lumbar puncture was performed (Sham operation group) was also prepared as a control.

Figure 8C:
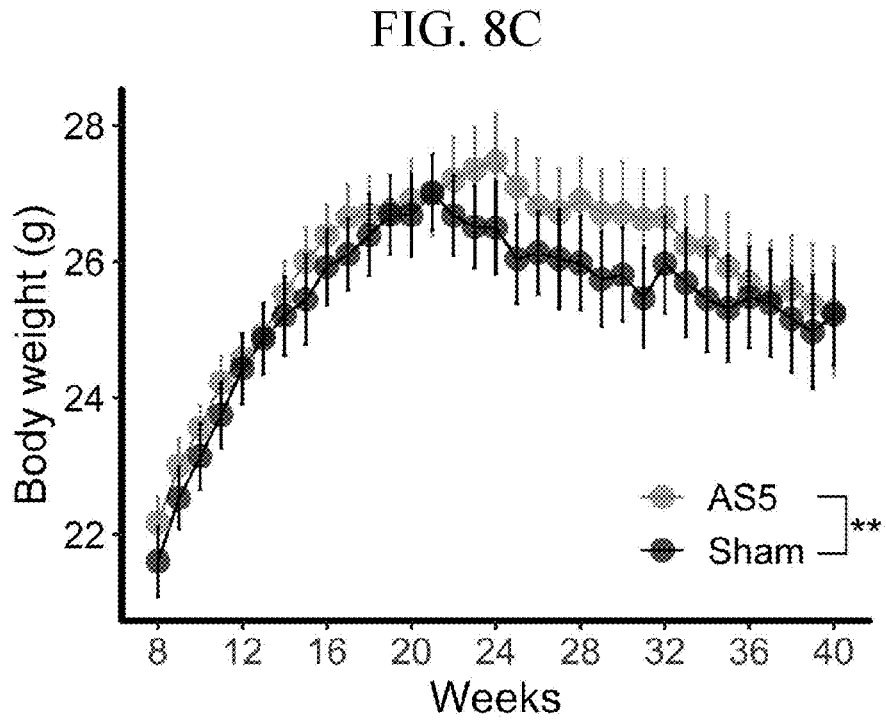
FIG. 8C is a graph showing changes in body weight over time in AS5-administered mice in Example 6.
Figure 8D:
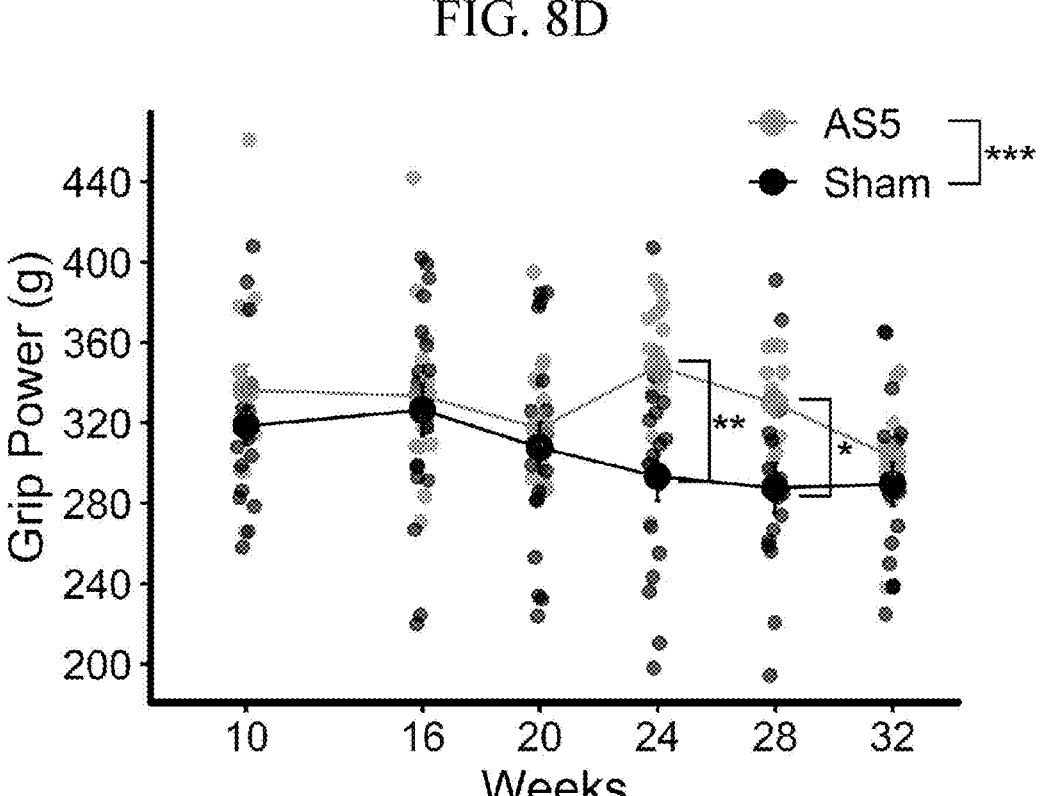
FIG. 8D is a graph showing changes in grip power over time in AS5-administered mice in Example 6.
Figure 8E:
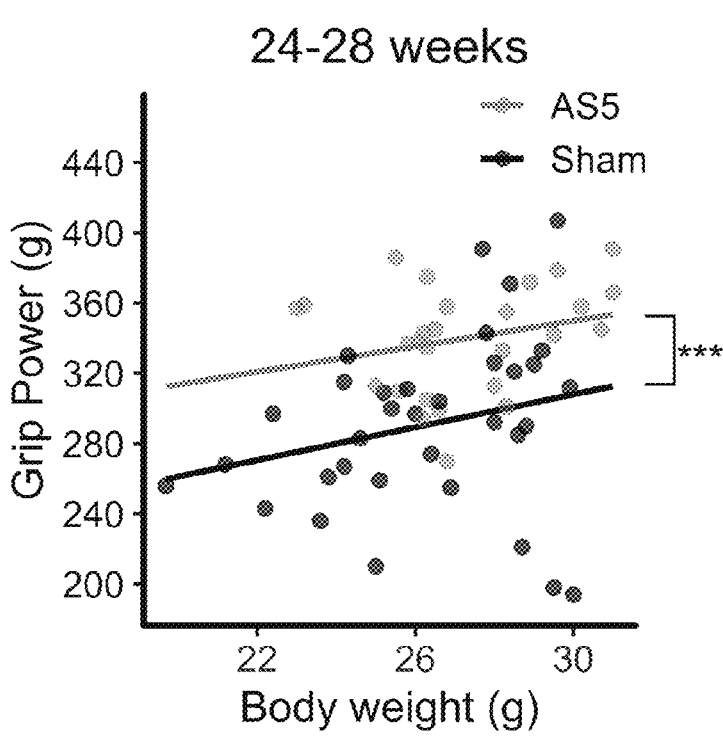
FIG. 8E is a graph showing the relationship between body weight and grip power in 24- to 28-week-old mice in Example 6.

In addition, the body weight and grip power of the mice subjected to the administration test were measured over time. The results are shown in FIG. 8C (body weight) and FIG. 8D (grip power). The relationship between body weight and grip power in 24- to 28-week-old mice is also shown in FIG. 8E.

In the observation up to 40 weeks of age, improvement in body weight change was observed in the AS5-administered group compared to the Sham operation group (two-way ANOVA; p-value 0.001; AS5-administered group: 12 mice, Sham surgery group: 16 mice) (see FIG. 8C). As for the motor function, improvement in grip strength was observed in the AS5-administered group at 24 weeks of age (two-tailed t-test; p-value: 0.001; AS5-administered group: 15 mice, Sham operation group: 18 mice) and 28 weeks of age (two-tailed t-test; p-value: 0.012; AS5-administered group: 12 mice, Sham operation group: 16 mice) (see FIG. 8D). Grip power at 24 and 28 weeks of age was significantly increased in the AS5-administered group even after body weight correction (analysis of covariance; p-value: 0.0001) (see FIG. 8E).

These results suggest that the antisense oligonucleotides that enhance alternative splicing of intron 6 of TDP-43 mRNA are effective for diseases exhibiting TDP-43 proteinopathy.

INDUSTRIAL APPLICABILITY

The antisense nucleic acid of the present embodiment can enhance the alternative splicing of intron 6 of TDP-43 mRNA. The alternative splicing enhancer of the present embodiment contains the antisense nucleic acid and can enhance the alternative splicing of intron 6 of TDP-43 mRNA. The pharmaceutical composition of the present embodiment contains the antisense nucleic acid and can prevent or treat TDP-43 proteinopathy. According to the screening method of the present embodiment, an alternative splicing enhancer of intron 6 of TDP-43 mRNA can be screened. According to the screening method of the present embodiment, a candidate compound for prevention or treatment of TDP-43 proteinopathy can be screened.

The invention claimed is:

1. An antisense oligonucleotide targeting intron 6 of TDP-43 pre-mRNA, comprising a nucleotide sequence that is fully complementary to 15 to 25 consecutive bases in a target sequence, wherein the target sequence is the 96th to 330th or 400th to 530th positions of a nucleotide sequence represented by SEQ ID NO:1.

2. The antisense oligonucleotide according to claim 1, comprising a nucleotide sequence represented by any one of SEQ ID NOS: 2 to 7.

3. An alternative splicing enhancer of intron 6 of TDP-43 pre-mRNA, comprising the antisense oligonucleotide according to claim 1 as an active ingredient.

4. A pharmaceutical composition, comprising the antisense oligonucleotide according to claim 1 as an active ingredient, wherein the pharmaceutical composition is used for prevention or treatment of TDP-43 proteinopathy.

5. The pharmaceutical composition according to claim 4, wherein the TDP-43 proteinopathy is frontotemporal lobar degeneration or amyotrophic lateral sclerosis.

6. A screening method for an alternative splicing enhancer of intron 6 of TDP-43 mRNA, comprising culturing CSE1L-knockdown cells expressing TDP-43 mRNA in the presence of a test substance, and quantifying splicing variants not including intron 6 and splicing variants including intron 6 among the TDP-43 mRNA in the cells, wherein a decrease in expression level of the splicing variants including intron 6 in the presence of the test substance compared to that in the absence of the test substance indicates that the test substance is a candidate for the alternative splicing enhancer of intron 6 of TDP-43 mRNA.

7. A screening method for a candidate compound for prevention or treatment of TDP-43 proteinopathy, comprising culturing CSE1L-knockdown cells expressing TDP-43 mRNA in the presence of a test substance, and quantifying splicing variants not including intron 6 and splicing variants including intron 6 among the TDP-43 mRNA in the cells, wherein a decrease in expression level of the splicing variants including intron 6 in the presence of the test substance compared to that in the absence of the test substance indicates that the test substance is a candidate compound for prevention or treatment of TDP-43 proteinopathy.

* * * * *

SEQUENCE LISTING

<160> NUMBER OF SEQ ID NOS: 33

<210> SEQ ID NO 1
<211> LENGTH: 1015
<212> TYPE: DNA
<213> ORGANISM: Homo sapiens

<400> SEQUENCE: 1
atatccaatg ccgaacctaa gcacaatagc aatagacagt tagaaagaag tggaagattt        60
ggtggtaatc caggtggctt tgggaatcag ggtggatttg gtaatagcag aggggggtgga      120 gctggtttgg gaaacaatca aggtagtaat atgggtggtg ggatgaactt tggtgcgttc       180
agcattaatc cagccatgat ggctgccgcc caggcagcac tacagagcag ttggggtatg       240
atgggcatgt tagccagcca gcagaaccag tcaggcccat cgggtaataa ccaaaaccaa       300
ggcaacatgc agagggagcc aaaccaggcc ttcggttctg gaaataactc ttatagtggc       360
tctaattctg gtgcagcaat tggttgggga tcagcatcca atgcagggtc gggcagtggt       420
tttaatggag gctttggctc aagcatggat tctaagtctt ctggctgggg aatgtagaca       480
gtggggttgt ggttggttgg tatagaatgg tgggaattca aattttttcta aactcatggt     540 aagtatattg taaaatacat atgtactaag aattttcaaa attggtttgt tcagtgtgga       600
gtatattcag cagtattttt gacatttttc tttagaaaaa ggaagagcta aaggaatttt       660
ataagttttg ttacatgaaa ggttgaaata ttgagtggtt gaaagtgaac tgctgtttgc       720
ctgattggta aaccaacaca ctacaattga tatcaaaagg tttctcctgt aatattttat       780
ccctggactt gtcaagtgaa ttctttgcat gttcaaaacg gaaaccattg attagaacta       840
cattctttac cccttgtttt aatttgaacc ccaccatatg gatttttttc cttaagaaaa       900 tctccttta ggagatcatg gtgtcacagt gtttggttct tttgttttgt tttttaacac        960
ttgtctcccc tcatacacaa aagtacaata tgaagccttc atttaatctc tgcag          1015

<210> SEQ ID NO 2
<211> LENGTH: 25
<212> TYPE: DNA
<213> ORGANISM: Artificial Sequence
<220> FEATURE:
<223> OTHER INFORMATION: Synthetic nucleotides for AS2

<400> SEQUENCE: 2 tccacccccct ctgctattac caaat                                             25

<210> SEQ ID NO 3
<211> LENGTH: 25
<212> TYPE: DNA
<213> ORGANISM: Artificial Sequence
<220> FEATURE:
<223> OTHER INFORMATION: Synthetic nucleotides for AS4

<400> SEQUENCE: 3
tgctgaacgc accaaagttc atccc                                             25

<210> SEQ ID NO 4
<211> LENGTH: 25
<212> TYPE: DNA
<213> ORGANISM: Artificial Sequence
<220> FEATURE:
<223> OTHER INFORMATION: Synthetic nucleotides for AS5

<400> SEQUENCE: 4
gctaacatgc ccatcatacc ccaac                                             25

-continued

```
<210> SEQ ID NO 5
<211> LENGTH: 24
<212> TYPE: DNA
<213> ORGANISM: Artificial Sequence
<220> FEATURE:
<223> OTHER INFORMATION: Synthetic nucleotides for AS5.1

<400> SEQUENCE: 5
cataccccaa ctgctctgta gtgc                                           24

<210> SEQ ID NO 6
<211> LENGTH: 25
<212> TYPE: DNA
<213> ORGANISM: Artificial Sequence
<220> FEATURE:
<223> OTHER INFORMATION: Synthetic nucleotides for AS5.2

<400> SEQUENCE: 6
ggttttggtt attacccgat gggcc                                          25

<210> SEQ ID NO 7
<211> LENGTH: 25
<212> TYPE: DNA
<213> ORGANISM: Artificial Sequence
<220> FEATURE:
<223> OTHER INFORMATION: Synthetic nucleotides for AS6.1

<400> SEQUENCE: 7
gcctccatta aaaccactgc ccgac                                          25

<210> SEQ ID NO 8
<211> LENGTH: 20
<212> TYPE: DNA
<213> ORGANISM: Artificial Sequence
<220> FEATURE:
<223> OTHER INFORMATION: Synthetic nucleotides for forward primer of
      TDP-43 mRNA intron 6

<400> SEQUENCE: 8
gcgctgtaca gaggacatga                                                20

<210> SEQ ID NO 9
<211> LENGTH: 18
<212> TYPE: DNA
<213> ORGANISM: Artificial Sequence
<220> FEATURE:
<223> OTHER INFORMATION: Synthetic nucleotides for reverse primer of
      TDP-43 mRNA intron 6

<400> SEQUENCE: 9
gcctgtgatg cgtgatga                                                  18

<210> SEQ ID NO 10
<211> LENGTH: 20
<212> TYPE: DNA
<213> ORGANISM: Artificial Sequence
<220> FEATURE:
<223> OTHER INFORMATION: Synthetic nucleotides for reverse primer of
      TDP-43 mRNA intron 6

<400> SEQUENCE: 10
agttccatct caaaagggtc                                                20

<210> SEQ ID NO 11
<211> LENGTH: 25
```

-continued

```
<212> TYPE: DNA
<213> ORGANISM: Artificial Sequence
<220> FEATURE:
<223> OTHER INFORMATION: Synthetic nucleotides for AS1

<400> SEQUENCE: 11
aagccacctg gattaccacc aaatc                                          25

<210> SEQ ID NO 12
<211> LENGTH: 25
<212> TYPE: DNA
<213> ORGANISM: Artificial Sequence
<220> FEATURE:
<223> OTHER INFORMATION: Synthetic nucleotides for AS2.1

<400> SEQUENCE: 12
cctctgctat taccaaatcc accct                                          25

<210> SEQ ID NO 13
<211> LENGTH: 25
<212> TYPE: DNA
<213> ORGANISM: Artificial Sequence
<220> FEATURE:
<223> OTHER INFORMATION: Synthetic nucleotides for AS3

<400> SEQUENCE: 13
tgattgtttc ccaaaccagc tccac                                          25

<210> SEQ ID NO 14
<211> LENGTH: 25
<212> TYPE: DNA
<213> ORGANISM: Artificial Sequence
<220> FEATURE:
<223> OTHER INFORMATION: Synthetic nucleotides for AS6

<400> SEQUENCE: 14
aattgctgca ccagaattag agcca                                          25

<210> SEQ ID NO 15
<211> LENGTH: 25
<212> TYPE: DNA
<213> ORGANISM: Artificial Sequence
<220> FEATURE:
<223> OTHER INFORMATION: Synthetic nucleotides for AS7

<400> SEQUENCE: 15
actccatgaa ataaagagta gcgga                                          25

<210> SEQ ID NO 16
<211> LENGTH: 20
<212> TYPE: DNA
<213> ORGANISM: Artificial Sequence
<220> FEATURE:
<223> OTHER INFORMATION: Synthetic nucleotides for forward primer of
     TDP-43 mRNA intron 6

<400> SEQUENCE: 16
cagagctttt gccttcgtca                                                20

<210> SEQ ID NO 17
<211> LENGTH: 18
<212> TYPE: DNA
<213> ORGANISM: Artificial Sequence
<220> FEATURE:
<223> OTHER INFORMATION: Synthetic nucleotides for reverse primer of
     TDP-43 mRNA intron 6
```

-continued

```
<400> SEQUENCE: 17
caaagacgca gcctgtgc                                                    18

<210> SEQ ID NO 18
<211> LENGTH: 22
<212> TYPE: DNA
<213> ORGANISM: Artificial Sequence
<220> FEATURE:
<223> OTHER INFORMATION: Synthetic nucleotides for forward primer of
      TDP-43 mRNA exon3-4

<400> SEQUENCE: 18
aactgagcag gatctgaaag ac                                               22

<210> SEQ ID NO 19
<211> LENGTH: 21
<212> TYPE: DNA
<213> ORGANISM: Artificial Sequence
<220> FEATURE:
<223> OTHER INFORMATION: Synthetic nucleotides for reverse primer of
      TDP-43 mRNA exon3-4

<400> SEQUENCE: 19
cgaacaaagc caaacccttt c                                                21

<210> SEQ ID NO 20
<211> LENGTH: 9
<212> TYPE: DNA
<213> ORGANISM: Artificial Sequence
<220> FEATURE:
<223> OTHER INFORMATION: Synthetic nucleotides for a part of probe
      (5' region) of TDP-43 mRNA exon 3-4

<400> SEQUENCE: 20 tggagaggt                                                              9

<210> SEQ ID NO 21
<211> LENGTH: 17
<212> TYPE: DNA
<213> ORGANISM: Artificial Sequence
<220> FEATURE:
<223> OTHER INFORMATION: Synthetic nucleotides for a part of probe
      (3' region) of TDP-43 mRNA exon 3-4

<400> SEQUENCE: 21
tcttatggtt caggtca                                                     17

<210> SEQ ID NO 22
<211> LENGTH: 19
<212> TYPE: DNA
<213> ORGANISM: Artificial Sequence
<220> FEATURE:
<223> OTHER INFORMATION: Synthetic nucleotides for forward primer of
      TDP-43 mRNA intron 6

<400> SEQUENCE: 22
aggtggcttt gggaatcag                                                   19

<210> SEQ ID NO 23
<211> LENGTH: 20
<212> TYPE: DNA
<213> ORGANISM: Artificial Sequence
<220> FEATURE:
<223> OTHER INFORMATION: Synthetic nucleotides for reverse primer of
      TDP-43 mRNA intron 6

<400> SEQUENCE: 23
```
caccaaagtt catccctcca                                                               20

<210> SEQ ID NO 24
<211> LENGTH: 9
<212> TYPE: DNA
<213> ORGANISM: Artificial Sequence
<220> FEATURE:
<223> OTHER INFORMATION: Synthetic nucleotides for a part of probe
      (5' region) of TDP-43 mRNA intron 6

<400> SEQUENCE: 24 tggagctgg                                                                           9

<210> SEQ ID NO 25
<211> LENGTH: 15
<212> TYPE: DNA
<213> ORGANISM: Artificial Sequence
<220> FEATURE:
<223> OTHER INFORMATION: Synthetic nucleotides for a part of probe
      (3' region) of TDP-43 mRNA intron 6

<400> SEQUENCE: 25
cttgggaaat aacca                                                                    15

<210> SEQ ID NO 26
<211> LENGTH: 21
<212> TYPE: DNA
<213> ORGANISM: Artificial Sequence
<220> FEATURE:
<223> OTHER INFORMATION: Synthetic nucleotides for forward primer of
      TDP-43 mRNA intron 7

<400> SEQUENCE: 26
tgctgtatgg tgtgtgttct c                                                             21

<210> SEQ ID NO 27
<211> LENGTH: 20
<212> TYPE: DNA
<213> ORGANISM: Artificial Sequence
<220> FEATURE:
<223> OTHER INFORMATION: Synthetic nucleotides for reverse primer of
      TDP-43 mRNA intron 7

<400> SEQUENCE: 27
ccacaagctc agtccatgtt                                                               20

<210> SEQ ID NO 28
<211> LENGTH: 9
<212> TYPE: DNA
<213> ORGANISM: Artificial Sequence
<220> FEATURE:
<223> OTHER INFORMATION: Synthetic nucleotides for a part of probe
      (5' region) of TDP-43 mRNA intron 7

<400> SEQUENCE: 28 agtgtggga                                                                           9

<210> SEQ ID NO 29
<211> LENGTH: 15
<212> TYPE: DNA
<213> ORGANISM: Artificial Sequence
<220> FEATURE:
<223> OTHER INFORMATION: Synthetic nucleotides for a part of probe
      (3' region) of TDP-43 mRNA intron 7

<400> SEQUENCE: 29

-continued

```
acgtgaactg aagct                                                                    15

<210> SEQ ID NO 30
<211> LENGTH: 20
<212> TYPE: DNA
<213> ORGANISM: Artificial Sequence
<220> FEATURE:
<223> OTHER INFORMATION: Synthetic nucleotides for forward primer of
      GAPDH

<400> SEQUENCE: 30
tgtgtccgtc gtggatctga                                                               20

<210> SEQ ID NO 31
<211> LENGTH: 21
<212> TYPE: DNA
<213> ORGANISM: Artificial Sequence
<220> FEATURE:
<223> OTHER INFORMATION: Synthetic nucleotides for reverse primer of
      GAPDH

<400> SEQUENCE: 31
ttgctgttga agtcgcagga g                                                             21

<210> SEQ ID NO 32
<211> LENGTH: 20
<212> TYPE: DNA
<213> ORGANISM: Artificial Sequence
<220> FEATURE:
<223> OTHER INFORMATION: Synthetic nucleotides for forward primer of
      Aif1

<400> SEQUENCE: 32
acgaaccctc tgatgtggtc                                                               20

<210> SEQ ID NO 33
<211> LENGTH: 19
<212> TYPE: DNA
<213> ORGANISM: Artificial Sequence
<220> FEATURE:
<223> OTHER INFORMATION: Synthetic nucleotides for reverse primer of
      Aif1

<400> SEQUENCE: 33
cgggatggaa gagagagga                                                                19
```